(12) United States Patent
Bell et al.

(10) Patent No.: US 7,858,605 B2
(45) Date of Patent: Dec. 28, 2010

(54) ORAL CONTRACEPTIVES TO PREVENT PREGNANCY AND DIMINISH PREMENSTRUAL SYMPTOMATOLOGY

(75) Inventors: Robert G. Bell, Palm Harbor, FL (US); Carole Ben-Maimon, Merion, PA (US); Beata Iskold, Livingston, NJ (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 201 days.

(21) Appl. No.: 11/951,492

(22) Filed: Dec. 6, 2007

(65) Prior Publication Data

US 2008/0132473 A1 Jun. 5, 2008

Related U.S. Application Data

(62) Division of application No. 10/309,313, filed on Dec. 4, 2002, now Pat. No. 7,320,969.

(60) Provisional application No. 60/335,807, filed on Dec. 5, 2001.

(51) Int. Cl.
*A61K 31/56* (2006.01)
(52) U.S. Cl. .................................................. 514/170
(58) Field of Classification Search .................. 514/170
See application file for complete search history.

(56) References Cited

U.S. PATENT DOCUMENTS

| | | |
|---|---|---|
| 3,568,828 A | 3/1971 | Lerner |
| 4,145,416 A | 3/1979 | Lachnit-Fixson et al. |
| 4,171,358 A | 10/1979 | Black |
| 4,215,691 A | 8/1980 | Wong |
| 4,291,014 A | 9/1981 | Keith et al. |
| 4,292,315 A | 9/1981 | Vorys |
| 4,390,531 A | 6/1983 | Edgren |
| 4,438,139 A | 3/1984 | Keith et al. |
| 4,530,839 A | 7/1985 | Pasquale |
| 4,534,468 A | 8/1985 | Nuckols et al. |
| 4,544,554 A | 10/1985 | Pasquale |
| 4,616,006 A | 10/1986 | Pasquale |
| 4,628,051 A | 12/1986 | Pasquale |
| 4,685,911 A | 8/1987 | Konno et al. |
| 4,736,849 A | 4/1988 | Leonard et al. |
| 4,752,478 A | 6/1988 | Bondi et al. |
| 4,762,717 A | 8/1988 | Crowley, Jr. |
| 4,962,098 A | 10/1990 | Boissonneault |
| 4,971,998 A | 11/1990 | Wurtman et al. |
| 5,010,070 A | 4/1991 | Boissonneault |
| 5,043,331 A | 8/1991 | Hirvonen et al. |
| 5,098,714 A | 3/1992 | Wright et al. |
| 5,108,995 A | 4/1992 | Casper |
| 5,208,225 A | 5/1993 | Boissonneault et al. |
| 5,256,421 A | 10/1993 | Casper |
| 5,262,408 A | 11/1993 | Bergink |
| 5,276,022 A | 1/1994 | Casper |
| 5,280,023 A | 1/1994 | Ehrlich et al. |
| 5,340,584 A | 8/1994 | Spicer et al. |
| 5,382,573 A | 1/1995 | Casper |
| 5,510,341 A | 4/1996 | Ehrlich et al. |
| 5,552,394 A | 9/1996 | Hodgen |
| 5,567,695 A | 10/1996 | Labrie |
| 5,585,370 A | 12/1996 | Casper |
| 5,633,242 A | 5/1997 | Oettel et al. |
| 5,662,927 A | 9/1997 | Ehrlich et al. |
| RE35,724 E * | 2/1998 | Pasquale ..................... 514/170 |
| 5,747,480 A | 5/1998 | Gast |
| 5,753,639 A | 5/1998 | Labrie |
| 5,756,490 A | 5/1998 | Lachnit et al. |
| 5,827,843 A | 10/1998 | Koninckx |
| 5,858,405 A | 1/1999 | Gast |
| 5,891,867 A | 4/1999 | Lanquetin et al. |
| 5,898,032 A * | 4/1999 | Hodgen ..................... 514/178 |
| RE36,247 E | 7/1999 | Plunkett et al. |
| 5,980,940 A | 11/1999 | Spona et al. |
| 6,027,749 A | 2/2000 | Schmidt-Gollwitzer et al. |
| 6,028,064 A | 2/2000 | Rodriguez et al. |
| 6,139,873 A | 10/2000 | Hughes, Jr. et al. |
| 6,214,815 B1 | 4/2001 | Shangold et al. |
| 6,251,956 B1 | 6/2001 | Kafrissen et al. |
| 6,265,393 B1 | 7/2001 | Heinrichs |

(Continued)

FOREIGN PATENT DOCUMENTS

| | | |
|---|---|---|
| CN | 1189101 A | 7/1998 |
| EP | 0 253 607 A1 | 1/1988 |
| EP | 0 911 029 B1 | 4/2002 |
| WO | WO 93/17686 A1 | 9/1993 |
| WO | WO 98/04246 A2 | 2/1998 |

(Continued)

OTHER PUBLICATIONS

Davies, G.C., et al., "Ovarian Activity and Bleeding Patterns During Extended Continuous Use of a Combined Contraceptive Vaginal Ring," *Contraception* 46:269-278, Elsevier (1992).

(Continued)

*Primary Examiner*—San-ming Hui
(74) *Attorney, Agent, or Firm*—Sterne, Kessler, Goldstein & Fox P.L.L.C.

(57) ABSTRACT

This invention relates to a method of preventing pregnancy and treating PMS including PMDD. More particularly, the invention relates to a method, which involves administering one of several combination oral contraceptive regimens in combination with an antidepressant and a kit containing the same.

30 Claims, No Drawings

U.S. PATENT DOCUMENTS

| | | | |
|---|---|---|---|
| 6,306,914 | B1 | 10/2001 | de Ziegler et al. |
| 6,312,722 | B1 | 11/2001 | Schmidt-Gollwitzer et al. |
| 6,319,911 | B1 | 11/2001 | Rodriguez |
| RE37,838 | E | 9/2002 | Spona et al. |
| 6,451,779 | B1 | 9/2002 | Hesch |
| 6,479,475 | B1 | 11/2002 | Gast |
| 6,500,814 | B1 | 12/2002 | Hesch |
| 6,511,970 | B1 | 1/2003 | Rodriguez |
| 6,765,002 | B2 | 7/2004 | Rodriguez |
| 6,787,531 | B1 | 9/2004 | Hilman et al. |
| 7,150,355 | B2 | 12/2006 | Coe et al. |
| RE39,861 | E | 9/2007 | Hodgen |
| 7,320,969 | B2 | 1/2008 | Bell et al. |
| 7,427,609 | B2 | 9/2008 | Leonard |
| 2001/0044431 | A1 | 11/2001 | Rodriguez |
| 2002/0132801 | A1 | 9/2002 | Heil et al. |
| 2003/0018018 | A1 | 1/2003 | Hodgen et al. |
| 2003/0114429 | A1 | 6/2003 | Hilman et al. |
| 2003/0119798 | A1 | 6/2003 | Heil et al. |
| 2003/0144258 | A1 | 7/2003 | Heil et al. |
| 2003/0216366 | A1 | 11/2003 | Leonard et al. |
| 2003/0229057 | A1 | 12/2003 | Caubel et al. |
| 2004/0009960 | A1 | 1/2004 | Heil et al. |
| 2004/0142914 | A1 | 7/2004 | Friedman et al. |
| 2004/0220152 | A1 | 11/2004 | Ben-Maimon et al. |
| 2004/0222123 | A1 | 11/2004 | Niemann |
| 2004/0251301 | A1 | 12/2004 | Niemann et al. |
| 2005/0064031 | A1 | 3/2005 | Stockemann et al. |
| 2005/0143359 | A1 | 6/2005 | Bell et al. |
| 2006/0135496 | A1 | 6/2006 | DiLiberti et al. |
| 2007/0111975 | A1 | 5/2007 | DiLiberti et al. |
| 2007/0158233 | A1 | 7/2007 | Coe et al. |
| 2008/0064670 | A1 | 3/2008 | Bell et al. |
| 2008/0125402 | A1 | 5/2008 | DiLiberti et al. |

FOREIGN PATENT DOCUMENTS

| | | |
|---|---|---|
| WO | WO 98/04266 A1 | 2/1998 |
| WO | WO 98/04267 A1 | 2/1998 |
| WO | WO 00/38691 A1 | 7/2000 |
| WO | WO 02/03975 A2 | 1/2002 |
| WO | WO 2004/080442 A1 | 9/2004 |
| WO | WO 2005/032558 A1 | 4/2005 |

OTHER PUBLICATIONS

Hillard, P.J., "Oral contraception noncompliance: the extent of the problem," *Adv. Contracept.* 8:13-20, Kluwer Academic (1992).

Koetsawang, S., et al., "A randomized, double-blind study of six combined oral contraceptives," *Contraception* 25:231-241, Elsevier (1982).

Rosenberg, M.J., and Waugh, M.S., "Oral contraceptive discontinuation: a prospective evaluation of frequency and reasons," *Am. J. Obstet. Gynecol.* 179:577-582, Elsevier (1998).

Threlkeld, D.S., ed., "Oral Contraceptives," in *Drug Facts and Comparisons*, Facts and Comparisons, St. Louis, MO, pp. 257-268 (1985).

Walker, A., and, Bancroft, J., "Relationship Between Premenstrual Symptoms and Oral Contraceptive Use: A Controlled Study," Psychosom. Med. 52:86-96, Lippincott Williams & Wilkins (1990).

Ware, M., et al., ed., "Oral Contraception and Depression," *Br. Med. J.* 4:380-381, British Medical Association (1969).

World Health Organization Scientific Group, "8. Risks With Particular Reference to Neoplasia of Therapeutic Estrogens and Progestins Given to Peri- and Postmenopausal Women," in *Research on the Menopause*, World Health Organization, Geneva, Switzerland, pp. 52-69 (1981).

International Preliminary Examination Report for International Application No. PCT/US02/38602, completed on Jul. 9, 2004, European Patent Office, Munich, Germany.

International Search Report for International Application No. PCT/US04/013589, mailed on Mar. 9, 2006, U.S. Patent Office, Alexandria, Virginia.

Written Opinion for International Application No. PCT/US04/013589, completed on Nov. 11, 2005, Alexandria, Virginia.

Written Opinion for International Application No. PCT/US04/22829, completed on Sep. 18, 2006, U.S. Patent Office, Alexandria, Virginia.

Co-pending U.S. Appl. No. 12/162,445, inventors DiLiberti and Reape, filed Jan. 29, 2007 (Not Yet Published).

American Psychiatric Association, "Premenstrual Dysphoric Disorder," in *DSM-IV™: Diagnostic and Statistical Manual of Mental Disorders*, 4$^{th}$ edition, American Psychiatric Association, Washington, DC, pp. 715-718 (1994).

Annex I of Declaration of Dr. Anne Szarewski (Document D27 in the Opposition to European Patent No. EP 0 911 029 B1), Szarewski, A.M., *Curriculum Vitae*, 14 pages.

Annex II of Declaration of Dr. Anne Szarewski (Document D27 in the Opposition to European Patent No. EP 0 911 029 B1), "Commercially Available Monophasic Combined Oral Contraceptive Pills," and "Ratio of equivalence given in patent EP 0 911 029 B1".

Annex III of Declaration of Dr. Anne Szarewski (Document D27 in Opposition to European Patent No. EP 0 911 029 B1), Belsey, E.M., "The Association Between Vaginal Bleeding Patterns and Reasons for Discontinuation of Contraceptive Use," *Contraception* 38:207-225, Elsevier (1988).

Annex IV of Declaration of Dr. Anne Szarewski (Document D27 in Opposition to European Patent No. EP 0 911 029 B1), Benagiano, G. and Fraser, I., "The Depo-Provera Debate, Commentary on the Article Depo-Provera, A Critical Analysis," in: *Contraception* 24:493-528, Elsevier (1981).

Annex V of Declaration of Dr. Anne Szarewski (Document D27 in Opposition to European Patent No. EP 0 911 029 B1), "Is Cerazette the minipill of choice?," *Drug Ther. Bull.* 41:1-3, Consumers' Association (Sep. 2003).

Annex VI of Declaration of Dr. Anne Szarewski (Document D27 in Opposition to European Patent No. EP 0 911 029 B1), Committee for Proprietary Medicinal Products, "Clinical Investigation of Steroid Contraceptives in Women," *Note for Guidance on Clinical Investigation of Steroid Contraceptives in Women*, 5 pages, The European Agency for the Evaluation of Medicinal Products (Feb. 2000).

Annex VII of Declaration of Dr. Anne Szarewski (Document D27 in Opposition to European Patent No. EP 0 911 029 B1), Goldzieher, J.W. and Fotherby, K., eds., *Pharmacology of the Contraceptive Steroids*, Raven Press, New York, NY, pp. 82-86 (1994).

Annex VIII of Declaration of Dr. Anne Szarewski (Document D27 in Opposition to European Patent No. EP 0 911 029 B1), Guillebaud, J., ed., "The pill: how do I take it?," in: *The Pill and Other Hormones for Contraception*, Oxford University Press, Great Britain, UK, pp. 52-53, 110-113, 182-183, 190-191 (1991).

Annex IX of Declaration of Dr. Anne Szarewski (Document D27 in Opposition to European Patent No. EP 0 911 029 B1), Adams Hillard, P.J., "The patient's reaction to side effects of oral contraceptives," *Am. J. Obstet. Gynecol.* 161:1412-1415, Mosby-Year Book (1989).

Annex X of Declaration of Dr. Anne Szarewski (Document D27 in Opposition to European Patent No. EP 0 911 029 B1), International Working Group, "A consensus statement: enhancing patient compliance and oral contraceptive efficacy," *Brit. J. Fam. Planning* 18:126-129, Faculty of Family Planning and Reproductive Health Care (1993).

Annex XI of Declaration of Dr. Anne Szarewski (Document D27 in Opposition to European Patent No. EP 0 911 029 B1), Korver, T., for the Collaborative Study Group, "A double-blind study comparing the contraceptive efficacy, acceptability and safety of two progestogen-only pills containing desogestrel 75 µg/day or levonorgestrel 30 µg/day," *Eur. J. Contra. Reprod. Health Care* 3:169-178, Parthenon Publishing (1998).

Annex XII of Declaration of Dr. Anne Szarewski (Document D27 in Opposition to European Patent No. EP 0 911 029 B1), Larsson, K.S. and Machin, D., "Predictability of the safety of hormonal contraceptives from canine toxicological studies," in: *Safety requirements for contraceptive steroids*, Michael D., ed., Cambridge University Press, Oxford, UK, pp. 230-269 (1989).

Annex XIII of Declaration of Dr. Anne Szarewski (Document D27 in Opposition to European Patent No. EP 0 911 029 B1), Lumbiganon, P., "Depot-medroxyprogesterone acetate (DMPA) and cancer of the endometrium and ovary," *Contraception 49*:203-209, Butterworth-Heinemann (1994).

Annex XIV of Declaration of Dr. Anne Szarewski (Document D27 in Opposition to European Patent No. EP 0 911 029 B1), Rice, C.F., et al., "A comparison of the inhibition inhibition of ovulation achieved by desogestrel 75 μg and levnorgestrel 30 μg daily," *Human Reprod. 14*:982-985, Oxford University Press (1999).

Annex XV of Declaration of Dr. Anne Szarewski (Document D27 in Opposition to European Patent No. EP 0 911 029 B1), Rosenberg, M. and Waugh, M.S., "Causes and consequences of oral contraceptive noncompliance," *Am. J. Obstet. Gnyecol. 180*:S276-S279, Mosby, Inc. (1999).

Annex XVI of Declaration of Dr. Anne Szarewski (Document D27 in Opposition to European Patent No. EP 0 911 029 B1), Rosenberg, M.J., et al., "Use and Misuse of Oral Contraceptives: Risk Indicators for Poor Pill Taking and Discontinuation," *Contraception 51*:283-288, Elsevier Science Inc. (1995).

Annex XVII of Declaration of Dr. Anne Szarewski (Document D27 in Opposition to European Patent No. EP 0 911 029 B1), Rosenfeld, A., et al., "The Food and Drug Administration and Medroxyprogesterone Acetate," *JAMA 249*:2922-2928, American Medical Association (1983).

Annex XVIII of Declaration of Dr. Anne Szarewski (Document D27 in Opposition to European Patent No. EP 0 911 029 B1), Szarewski, A., ed., "Figure 3.5 Oestrogen-dominant and progestogen-dominant pills," in: *Hormonal Contraception: A Women's Guide*, Macdonald Optima, pp. 45 (1991).

Annex XIX of Declaration of Dr. Anne Szarewski (Document D27 in Opposition to European Patent No. EP 0 911 029 B1), Szarewski, A. and Guillebaud, J., eds., "Which Pill will Suit me Best?," in: *Contraception, A User's Handbook*, Oxford University Press, pp. 43-72 (1994).

Annex XX of Declaration of Dr. Anne Szarewski (Document D27 in Opposition to European Patent No. EP 0 911 029 B1), Wilkinson, C. and Szarewski, A., eds., "Management of Breakthrough Bleeding," in: *Contraceptive Dilemmas*, Altman Publishing, St. Albans, England, pp. 4-7 (2003).

Annex XXI of Declaration of Dr. Anne Szarewski, (Document D27 in Opposition to European Patent No. EP 0 911 029 B1), WHO Collaborative Study Group, "Depot-Medroxyprogesterone Acetate (DMPA) and Risk of Endometrial Cancer," *Int. J. Cancer 49*:186-190, Wiley-Liss, Inc. (1991).

Annex XXII of Declaration of Dr. Anne Szarewski (Document D27 in Opposition to European Patent No. EP 0 911 029 B1), WHO Collaborative Study Group, "Breast cancer and depot-medroxyprogesterone acetate: a multinational study," *Lancet 338*:833-838, Lancet Publishing Company (1991).

Attachment 1, Letter from Andreas Görlich to Barr Laboratories, "Gynäkologische Sensation oder graue Theorie? Monatsblutung nur noch zweimal im Jahr—wie ist das möglich?," (Gesundheits-Magazin) Health Magazine, 1 page (1984).

Attachment 2, Letter from Andreas Görlich to Barr Laboratories, "Zwei Monatsblutungen pro Jahr sind genug. Gefordert ist die sog. Distanz-Pille," Medical Tribune/Gyne, 1 page (1983).

Attachment 3, Letter from Andreas Görlich to Barr Laboratories, "Zwei Monatsblutungen pro Jahr sind genug!" Medical Tribune, Austrian Edition, and Medical Tribune, Swiss Edition, 2 pages (1984).

Attachment 4, Letter from Andreas Görlich to Barr Laboratories, "Frauenarzt fordert: Schafft die sinniosen Monatsblutungen ab!" Cosmopolitan 9:177, 1 page (1984).

Cachrimanidou, A. C., et al., "Long-interval treatment regimen with a desogestrel-containing oral contraceptive," *Contraception 48*:205-216, Butterworth-Heinemann (1993).

Daugherty, J. E., "Treatment Strategies for Premenstural Syndrome," *Am. Family Physician 58*:183-192 and 2 page insert, American Academy of Family Physicians (1998).

de Voogd, W. S., "Postponement of Withdrawal Bleeding With a Monophasic Oral Contraceptive Containing Desogestrel and Ethinylestradiol," *Contraception 44*:107-112, Butterworth-Heinemann (1991).

Dickey, R. P., "Oral Contraception: Realizing the Promise by Overcoming the Pitfalls," *Individualizing Oral Contraceptive Therapy, OBG Management Supplement*, pp. 2-6, Watson Pharma, Inc. (Oct. 2000).

English language translation of Attachment 1 to Letter from Andreas Görlich to Barr Laboratories, "Gynecological Sensation or Gray Theory? Menstruation only twice a year how is that possible?," Health Magazine (1984).

English language translation of Attachments 2 and 3, Letter from Andreas Görlich to Barr Laboratories, "Two "Menstrual Periods" Per Year Are Enough," Medical Tribune/Gyne (1983).

English language translation of Attachment 4 to Letter from Andreas Görlich to Barr Laboratories, "Gynecologist issues challenge: away with senseless menstrual bleeding!," Cosmopolitan 9:177 (1984).

European Opposition Document D1, Cachrimanidou, A.-C., et al., "Long-interval treatment regimen with a desogestrel-containing oral contraceptive," *Contraception 48*:205-216, Butterworth-Heinemann (1993), cited in the Opposition to European Patent No. 0 911 029 B1.

European Opposition Document D2, Kovacs, G.T., et al., "A trimonthly regimen for oral contraceptives," *Brit. J. Fam. Planning 19*:274-275, Faculty of Family Planning and Reproductive Health Care (1994), cited in the Opposition to European Patent No. 0 911 029 B1.

European Opposition Document D3, Davies, G.C., et al., "Ovarian Activity and Bleeding Patterns During Extended Continuous Use of a Combined Contraceptive Vaginal Ring," *Conception 46*:269-278, Elsevier (1992), cited in the Opposition to European Patent No. 0 911 029 B1.

European Opposition Document D4, "Vier keer per jaar ongesteld," Intermediair, 2 pages, Intermediair (May 2002), cited in the Opposition to European Patent No. 0 911 029 B1.

European Opposition Document D5, Loudon, N.B., et al., "Acceptability of an oral contraceptive that reduces the frequency of menstruation: the tri-cycle pill regimen," *Brit. Med. J. 2*:487-490, British Medical Association (1977), cited in the Opposition to European Patent No. 0 911 029 B1.

European Opposition Document D6, Vollebregt, J.A., et al., "A Study on Postponement of Menses with Low-Dose Combined Oral Contraceptives—Outcome and Acceptability," *Adv. Contraception 1*:207, Abstract No. 19, Kluwer Academics (1985), cited in the Opposition to European Patent No. 0 911 029 B1.

European Opposition Document D7, Omtzigt, A.M. and Boerrigter, P.J., "The effect of 30 μg ethinylestradiol/75 μg gestodene and 20 μg ethinylestradiol/150 μg desogestrel on cycle control during normal and extended oral contraceptive intake," *Eur. J. Contracept. Reprod. Health Care 1*:155, Abstract No. FC70, Parthenon Publishing (1996), cited in the Opposition to European Patent No. 0 911 029 B1.

European Opposition Document D8, Szarewski, A. and Guillebaud, J., eds., *Contraception, A User's Handbook*, Oxford University Press, Oxford, UK, pp. 46, 53, 54, 84, 87 (1994), cited in the Opposition to European Patent No. 0 911 029 B1.

European Opposition Document D9, Schneider, H.P.G., et al., eds., "Empfängnis-verhütung," Urban & Schwarzenberg, Munich, Germany, pp. 7-8 (1996), cited in the Opposition to European Patent No. 0 911 029 B1.

European Opposition Document D10, Guillebaud, J., ed., "*Contraception. Your questions answered*," Churchill Livingstone, New York, NY, pp. 75, 131, 154-155 (1986), cited in the Opposition to European Patent No. 0 911 029 B1.

European Opposition Document D11, Mishell, D.R., Jr., "Oral Contraception: Past, Present, and Future Perspectives," *Int. J. Fertil. 36*: 7-18, MSP International (1991), cited in the Opposition to European Patent No. 0 911 029 B1.

European Opposition Document D12, de Voogd, W.S., "Postponement of Withdrawal Bleeding with a Monophasic Oral Contraceptive Containing Desogestrel and Ethinylestradiol," *Contraception 44*:107-112, Elsevier (1991), cited in the Opposition to European Patent No. 0 911 029 B1.

European Opposition Document D13, Rutter, W., et al., "Women's attitudes to withdrawal bleeding and their knowledge and beliefs about the oral contraceptive pill," *Med. J. Australia 149*:417-419, Australasian Medical Publishing Co. (1988), cited in the Opposition to European Patent No. 0 911 029 B1.

European Opposition Document D14, Sulak, P.J., et al., "Extending the Duration of Active Oral Contraceptive Pills to Manage Hormone Withdrawal Symptoms," *Obstet. & Gynecol. 89*:179-182, Lippincott, Williams & Wilkins (1997), cited in the Opposition to European Patent No. 0 911 029 B1.

European Opposition Document D15, U.S. Patent No. 5,552,394, Hodgen, G.D., issued Sep. 3 1996, cited in the Opposition to European Patent No. 0 911 029 B1.

European Opposition Document D16, Speroff, L., et al., eds., "Chapter 2. Oral Contraception," in: *A Clinical Guide for Contraception*, Lippincott, Williams & Wilkins, pp. 25-117 (Nov. 2000), cited in the Opposition to European Patent No. 0 911 029 B1.

European Opposition Document D17, Düsterberg, B., et al., "Terminal Half-lives in Plasma and Bioavailability of Norethisterone, Levonorgestrel, Cyproterone acetate and Gestodene in Rats, Beagles and Rhesus Monkeys," *Contraception 24*:673-383, Elsevier (1981), cited in the Opposition to European Patent No. 0 911 029 B1.

European Opposition Document D18, Düsterberg, B., et al., "Half-lives in Plasma and Bioavailability of Ethinylestradiol in Laboratory Animals," *Drug Res. 36*:1187-1190, Edititio Cantor (1986), cited in the Opposition to European Patent No. 0 911 029 B1.

European Opposition Document D19, WIPO International Publication No. 93/17686, published Sep. 16, 1993, cited in the Opposition to European Patent No. 0 911 029 B1.

European Opposition Document D20, Letter filed by Schering AG in Opposition to EP 0686037 B1, the Medical College of Hampton Roads, 5 pages (Aug. 2003), cited in the Opposition to European Patent No. 0 911 029 B1.

European Opposition Document D21, Hamerlynck, J.V.Th.H., et al., "Postponement of Withdrawal Bleeding in Women Using Low-Dose Combined Oral Contraceptives," *Contraception 35*:199-205, Elsevier (1987), cited in the Opposition to European Patent No. 0 911 029 B1.

European Opposition Document D22, Anderson, F.D. and Hait, H., "A multicenter, randomized study of an extended cycle oral contraceptive," *Contraception 68*:89-96, Elsevier (Aug. 2003), cited in the Opposition to European Patent No. 0 911 029 B1.

European Opposition Document D23, Report of Bleeding observed with Seasonale products as compared to conventional OC products, addendum to Anderson, F.D. and Hait, H., "A multicenter, randomized study of an extended cycle oral contraceptive," *Contraception 68*:89-96, Elsevier (Aug. 2003), 2 pages, cited in the Opposition to European Patent No. 0 911 029 B1.

European Opposition Document D24, Glaser, J., "Seasonale®, Market Research," carried out by Ziment Associates on behalf of Barr Laboratories, Inc. (Jan. 2003), 14 pages, cited in the Opposition to European Patent No. 0 911 029 B1.

European Opposition Document D25, "The 2003 Gallup Study of the Market for Oral Contraceptives," conducted by Multi-Sponsor Surveys, Inc., for Barr Laboratories, Inc., 17 pages (May 2003), cited in the Opposition to European Patent No. 0 911 029 B1.

European Opposition Document D26, Comparison of Seasonale with other birth control products, IMS Health, Market data from Jun. 2001-Jan. 2004, 4 pages, cited in the Opposition to European Patent No. 0 911 029 B1.

European Opposition Document D27, Declaration of Dr. Anne Szarewski, In the Matter of EP 0 911 029 B1, Medical College of Hampton Roads and Opposition Thereto by Schering AG, 8 pages, cited in the Opposition to European Patent No. 0 911 029 B1 (Apr. 2004).

European Opposition Document D28, SEA-301, Summary Statistics: Observed Total Number of Days of Unscheduled Bleeding and/or Spotting by Cycle, cited in the Opposition for European Patent No. 0 911 029 B1.

European Opposition Document D29, Letter from U.S. FDA to Barr Research, Inc., undated and redacted, cited in the Opposition to European Patent No. 0 911 029 B1.

European Opposition Document D30, European Patent No. 0 253 607 A1, published Jan. 20, 1988, cited in the Opposition to European Patent No. 0 911 029 B1.

European Opposition Document D31, Publicly available Food and Drug Administration papers relating to marketing authorization for Seasonale®, 347 pages, cited in the Opposition to Patent No. 0 911 029 B1 (publicly available Mar. 2004).

European Opposition Document D32, Facts About Seasonale®, 1 page, Barr Laboratories, Inc. (available after Sep. 5, 2003), cited in the Opposition to Patent No. 0 911 029 B1.

European Opposition Document D33, Seasonale® Product Brochure, 15 pages, Duramed Pharmaceuticals, Inc. (Jan. 2004), cited in the Opposition to Patent No. 0 911 029 B1.

European Opposition Document D34, Seasonale®, Product Description and Information, Duramed Pharmaceuticals, Inc., 39 pages (Sep. 2003), cited in the Opposition to Patent No. 0 911 029 B1.

European Opposition Document D35, Declaration by Alan H. DeCherney, M. D., 6 pages, submitted with Appellant's Grounds of Appeal in the Opposition to European Patent No. 0 911 029 B1 (Nov. 2004).

European Opposition Document D36, "Coolest Inventions 2003," *Time Magazine*, issue of Nov. 17, 2003, 26 pages, submitted with Appellant's Grounds of Appeal in the Opposition to European Patent No. 0 911 029 B1.

European Opposition Document, Appellant's Grounds of Appeal, with Main Request and First, Second, Third, Fourth, Fifth and Sixth Auxiliary Requests; 37 pages; submitted by Patentee in the Opposition to European Patent No. 0 911 029 B1 (Nov. 2004).

European Opposition Document, Decision revoking the European Patent No. EP B 0 911 029 (Article 102(1),(3)EPC), issued by European Patent Office in the Opposition to European Patent No. 0 911 029 B1, Netherlands, 41 pages (Jul. 1, 2004).

European Opposition Document, Further Submission, "Urgent—Oral Proceedings Scheduled for Jun. 8, 2004," submitted by Patentee in the Opposition to European Patent No. 0 911 029 B1, 2 pages (May 2004).

European Opposition Document, Further Submission, "Urgent: Oral Proceedings on Jun. 8, 2004," submitted by Akzo Nobel N.V. in the Opposition to European Patent No. 0 911 029 B1, 1 page (May 2004).

European Opposition Document, Further Submission, "Urgent—Oral Proceedings Jun. 8, 2004," submitted by Schering AG in the Opposition to European Patent No. 0 911 029 B1, 2 pages (May 2004).

European Opposition Document, Further Written Submissions, submitted by Schering AG in the Opposition to European Patent No. 0 911 029 B1, 17 pages (Apr. 2004).

European Opposition Document, Notice and Statement of Opposition, submitted by Schering AG in the Opposition to European Patent No. 0 911 029 B1, 32 pages (Jan. 2003).

European Opposition Document, Notice of Opposition (Article 99 and Rule 55 EPC), submitted by Akzo Nobel N.V. in the Opposition to European Patent No. 0 911 029 B1, 8 pages (Jan. 2002).

European Opposition Document, Response to Communication of Notices of Opposition, submitted by Patentee in the Opposition to European Patent No. 0 911 029 B1, 10 pages (Oct. 2003).

European Opposition Document, Summons to Attend Oral Proceedings Pursuant to Rule 71(1) EPC, issued by European Patent Office, Netherlands, in the Opposition to European Patent No. 0 911 029 B1, 1 page (Jan. 2004).

European Opposition Document, Written Submission, with new Main and Auxiliary Requests, submitted by Patentee in the Opposition to European Patent No. 0 911 029 B1, 23 pages (Apr. 2004).

Exhibit A of Declaration by Alan H. DeCherney, M.D. (European Opposition Document D35), *Curriculum Vitae*, Alan Hersh DeCherney, M.D., 54 pages, Dec. 2003, submitted with Appellant's Grounds of Appeal in the Opposition to European Patent No. 0 911 029 B1.

Frackiewicz, E.J., and Shiovitz, T.M., "Evaluation and Management of Premenstrual Syndrome and Premenstrual Dysphoric Disorder," *J. Am. Pharm. Assoc. 41*:437-447, American Pharmaceutical Association (May/Jun. 2001).

Freeman, E.W., et al., "Concurrent Use of Oral Contraceptives With Antidepressants for Premenstrual Syndromes," *J. Clin. Pschyopharmacol.* 21:540-542, Lippincott Williams & Wilkins (Oct. 2001).

Freeman, E.W., et al., "Evaluation of a unique oral contraceptive in the treatment of premenstrual dysphoric disorder," *J. Womens Health Gend. Based Med.* 10(6):561-569 (Jul./Aug. 2001), PubMed Abstract (PMID 11559453).

Goldzieher, J.W., "Use and Misuse of the Term Potency with Respect to Oral Contraceptives," *J. Reproductive Med.* 31:533-539, The Journal of Reproductive Medicine, Inc. (1986).

Graham, C.A., and Sherwin, B.B., "A prospective treatment study of premenstrual symptoms using a triphasic oral contraceptive," *J. Psychosom. Res.* 36(3):257-266 (1992), PubMed Abstract (PMID 1564678).

Hamerlynck, J.V.Th.H., et al., "Postponement of Withdrawal Bleeding in Women Using Low-Dose Combined Oral Contraceptives," *Contraception* 35:199-205, Geron-X, Inc. (1987).

"Headaches: OCs are 'guilty by association'," *Contraceptive Technology Update* 14(7):109-112, Thomson American Health Consultants (1993).

Hipkin, L.J., "The Induction of Amenorrhoea," *J. R. Army Med. Corps* 138:15-18, London Royal Army Medical Corps (1992).

International Search Report for International Appl. No. PCT/US02/38602, mailed Apr. 4, 2003, European Patent Office, Rijswijk, NL.

Katzung, Basic & Clinical Pharmacology, 6th ed., 1995, p. 619-623.

King, R.J.B., and Whitehead, M.I., "Assessment of the potency of orally administered progestins in women," *Fertility and Sterility* 46:1062-1066, Elsevier for the American Society for Reproductive Medicine (1986).

Kornaat, H., et al., "The Acceptance of a 7-Week Cycle With a Modern Low-Dose Oral Contraceptive (Minulet®)," *Contraception* 45:119-127, Butterworth-Heinemann (1992).

Kovacs, G.T., et al., "A trimonthly regimen for oral contraceptives," *Br. J. Fam. Plann.* 19:274-275, Faculty of Family Planning and Reproductive Health Care of the Royal College of Obstetricians and Gynaecologists (1994).

Kudrow, L., "The Relationship of Headache Frequency to Hormone Use in Migraine," *Headache* 15:36-40, Blackwell Science (1975).

Kuhl, H., "Comparative Pharmacology of Newer Progestogens," *Drugs* 51:189-215, ADIS International Ltd. (1996).

Kupper, C., and Loch, E.-G., "Prämenstruelles Syndrom," *Deutsche Apotheker Zeitung* 136:23-29, Deutcher Apotheker Verlag (1996).

Letter from Andreas Görlich to Barr Laboratories, Inc., entitled "Tablets against pregnancy 'Seasonale'," 3 pages (Jun. 2004).

Loudon, N.B., et al., "Acceptability of an oral contraceptive that reduces the frequency of menstruation: the tri-cycle pill regimen," *Br. Med. J.* 2:487-490, British Medical Association (1977).

Lundeen, S.G., et al., "Rat uterine complement C3 expression as a model for progesterone receptor modulators: characterization of the new progestin trimegestone," *J. Steroid Biochem. & Molec. Biol.* 78:137-143, Elsevier Science Ltd. (Aug. 2001).

Mashchak, C.A., et al., "Comparison of pharmacodynamic properties of various estrogen formulations," *Am. J. Obstet. Gynecol.* 144:511-518, The C.V. Mosby Co. (1982).

Merck Index, 11th ed., 1989, monograph 4112.

Miller, L., and Notter, K.M., "Menstrual Reduction With Extended Use of Combination Oral Contraceptive Pills: Randomized Controlled Trial," *Obstet. Gynecol.* 98:771-778, Lippincott, Williams & Wilkins (Nov. 2001).

Mortola, J.F., et al., "Diagnosis of Premenstrual Syndrome by a Simple, Prospective, and Reliable Instrument: The Calendar of Premenstrual Experiences," *Obstet. Gynecol.* 76:302-307, Elsevier Science Publishing Co., Inc. (1990).

Notice of Paragraph IV Certification letter on behalf of Watson Laboratories, Inc., from Barry S. White of Frommer Lawrence & Haug LLP to Bruce L. Downey of Barr Laboratories, Inc., 17 pages (Jun. 2004).

Partial English translation of European Opposition Document D4, "Having a period four times per year," Intermediair, 2 pages, Intermediair (May 2002), cited in the Opposition to European Patent No. 0 911 029 B1.

Philibert D., et al., "The Pharmacological profile of a novel norpregnane progestin (trimegestone)," *Gynecol. Endocrinol.* 13:316-326, Parthenon Publishing (1999).

Phillips, A., et al., "A Comparison of the Potencies and Activities of Progestogens Used in Contraceptives," *Contraception* 36:181-192, Geron-X, Inc. (1987).

Piper, J.M., and Kennedy, D.L., "Oral Contraceptives in the United States: Trends in Content and Potency," *Intl. J. Epidemiology* 16:215-221, Oxford University Press (1987).

Romano, S., et al., "The Role of Fluoxetine in the Treatment of Premenstrual Dysphoric Disorder," Clin. Ther. 21:615-633, Excerpta Medica, Inc. (1999).

Shearman, R.P., "Oral contraceptive agents," *Med. J. Australia* 144:201-205, Australasian Medical Publishing (1986).

Sheth, A., et al., "A Randomized, Double-Blind Study of Two Combined and Two Progestogen-Only Oral Contraceptives," *Contraception* 25:243-252, Geron-X, Inc. (1982).

Silberstein, S.D., and Merriam, G.R., "Physiology of the menstrual cycle," *Cephalalgia* 20:148-154, Blackwell Science Ltd. (Apr. 2000).

Stearns, S., "PMS and PMDD in the Domain of Mental Health Nursing," *J. Psychosoc. Nurs.* 39:16-27, Slack Incorporated (Jan. 2001).

Steiner, M., et al., "Fluoxetine in the Treatment of Premenstrual Dysphoria," *N. Engl. J. Med.* 332:1529-1534, Massachusetts Medical Society (1995).

Steiner, M., "Premenstrual Syndromes," *Annu. Rev. Med.* 48:447-455, Annual Reviews Inc. (1997).

Steiner, M., and Born, L., "Diagnosis and treatment of premenstrual dysphoric disorder: an update," *Int. Clin. Psychopharmacol.* 15 (*Suppl. 3*):S5-S17, Lippincott Williams & Wilkins (Nov. 2000).

Sulak, P.J., et al., "Acceptance of altering the standard 21-day/7-day oral contraceptive regimen to delay menses and reduce hormone withdrawal symptoms," *Am. J. Obstet. Gynecol.* 186:1142-1149, Mosby, Inc. (Jun. 2002).

Sulak, P.J., et al., "Extending the Duration of Active Oral Contraceptive Pills to Manage Hormone Withdrawal Symptoms," *Obstet. Gynecol.* 89:179-183, Elsevier Science Inc. (1997).

Sulak, P.J., et al., "Hormone Withdrawal Symptoms in Oral Contraceptive Users," *Obstet. Gynecol.* 95:261-266, Lippincott, Williams & Wilkins (Feb. 2000).

Whitty, C.W.M., et al., "The Effect of Oral Contraceptives on Migraine," *Lancet* 1:856-859, Lancet Publishing Company (1966).

Wysocki, S., et al., "Hormonal Contraceptives: Extending the Benefits," *Am. J. Nurse Practitioners* 6:19-29, American College of Nurse Practitioners (Nov./Dec. 2002).

Yonkers, K.A., "Antidepressants in the Treatment of Premenstrual Dysphoric Disorder," *J. Clin. Psychiatry* 58 (*Suppl. 14*):4-13, Physicians Postgraduate Press (1997).

Yonkers, K.A., "Medical Management of Premenstrual Dysphoric Disorder," *J. Gend. Specif. Med.* 2:55-60, Multimedia Healthcare (1999).

Docket Sheet for *Duramed Pharmaceuticals, Inc. v. Sandoz Inc.*, Civil Docket Case No. 3:07-CV-05940, U.S. District Court, District of New Jersey (Trenton), most recent entry date of Feb. 23, 2010, 24 pages.

Docket Sheet for *Teva Women's Health, Inc. v. Lupin, Ltd. et al*, Civil Docket Case No. 3:09-CV-05112, U.S. District Court, District of New Jersey (Trenton), most recent entry date of Mar. 22, 2010, 7 pages.

Docket Sheet for *Duramed Pharmaceuticals, Inc. v. Watson Laboratories, Inc. et al*, Civil Docket Case No. 3:08-CV-00116, U.S. District Court, District of Nevada (Reno), most recent entry date of Apr. 21, 2010, 60 pages.

"Order" in *Duramed Pharmaceuticals, Inc. v. Watson Laboratories, Inc. et al*, Civil Docket Case No. 3:08-CV-00116, U.S. District Court, District of Nevada (Reno), filed Mar. 31, 2010, 11 pages.

Docket Sheet for *Teva Women's Health, Inc. v. Lupin, Ltd. et al*, Civil Docket Case No. 2:10-CV-00603, U.S. District Court, District of New Jersey (Newark), most recent entry date of Apr. 12, 2010, 6 pages.

"*Answer and Counterclaims of Lupin Pharmaceuticals, Inc. and Lupin, Ltd.*" in *Teva Women's Health, Inc. v. Lupin, Ltd. et al*, Civil Docket Case No. 2:10- CV-00603, U.S. District Court, District of New Jersey (Newark), filed Mar. 19, 2010, 13 pages.

Docket Sheet for *Teva Women's Health, Inc.* v. *Mylan Pharmaceuticals, Inc. et al*, Civil Docket Case No. 2:10-CV-01235, U.S. District Court, District of New Jersey (Newark), most recent entry date of Apr. 28, 2010, 4 pages.

Docket Sheet for *Teva Women's Health, Inc.* v. *Lupin, Ltd. et al*, Civil Docket Case No. 2:10-CV-00080, U.S. District Court, District of New Jersey (Newark), most recent entry date of Apr. 30, 2010, 11 pages.

Docket Sheet for *Watson Laboratories, Inc.* v. *Teva Women's Health, Inc.*, Civil Docket Case No. 3:10-CV-00115, U.S. District Court, District of Nevada (Reno) most recent entry date of Mar. 31, 2010, 3 pages.

"Complaint for Declaratory Judgment of Patent Invalidity and Non-Infringement" in *Watson Laboratories, Inc.* v. *Teva Women's Health, Inc.*, Civil Docket Case No. 3:10-CV-00115, U.S. District Court, District of Nevada (Reno), filed Feb. 25, 2010, 8 pages.

Docket Sheet for *Teva Women's Health, Inc.* v. *Mylan Pharmaceuticals, Inc. et al*, Civil Docket Case No. 2:10-CV-01234, U.S. District Court, District of New Jersey (Newark), most recent entry date of Mar. 15, 2010, 3 pages.

Docket Sheet for *Duramed Pharmaceuticals, Inc.* v. *Sandoz Inc.*, Civil Docket Case No. 3:07-CV-05940, U.S. District Court, District of New Jersey (Trenton), most recent entry date of Jun. 30, 2010, 17 pages.

Docket Sheet for *Teva Women's Health, Inc.* v. *Lupin, Ltd. et al*, Civil Docket Case No. 2:10-CV-00603, U.S. District Court, District of New Jersey (Newark), most recent entry date of Jul. 27, 2010, 6 pages.

Docket Sheet for *Teva Women's Health, Inc.* v. *Mylan Pharmaceuticals, Inc. et al*, Civil Docket Case No. 2:10-CV-01235, U.S. District Court, District of New Jersey (Newark), most recent entry date of Jul. 30, 2010, 7 pages.

Docket Sheet for *Teva Women's Health, Inc.* v. *Lupin, Ltd. et al*, Civil Docket Case No. 2:10-CV-00080, U.S. District Court, District of New Jersey (Newark), most recent entry date of Aug. 9, 2010, 15 pages.

"Exhibit B" (Deposition of Howard Hait) to "Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Jul. 13, 2010, 92 pages.

"Exhibit D" (Deposition of Kathleen Z. Reape, M.D.) to "Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Jul. 13, 2010, 49 pages.

"Defendants Watson Laboratories, Inc. and Watson Pharmaceuticals, Inc. 's Brief in Opposition to Plaintiff's Motion to Dismiss/Strike Watson's Inequitable Conduct Counterclaim and Defense" in *Teva Women's Health, Inc.* v. *Lupin, Ltd. et al*, Consolidated Civil Docket Case Nos. 2:10-CV-00080 and 2:10-cv-01234, filed Jul. 23, 2010, 44 pages.

Docket Sheet for *Teva Women's Health, Inc.* v. *Mylan Pharmaceuticals, Inc. et al*, Civil Docket Case No. 2:10-CV-01234, U.S. District Court, District of New Jersey (Newark), most recent entry date of Aug. 9, 2010, 9 pages.

Docket Sheet for *Watson Laboratories, Inc.* v. *Teva Women's Health, Inc.*, Civil Docket Case No. 3:10-CV-00115, U.S. District Court, District of Nevada (Reno) most recent entry date of May 19, 2010, 2 pages.

Docket Sheet for *Duramed Pharmaceuticals, Inc.* v. *Watson Laboratories, Inc.*, Case No. 10-1331, U.S. Court of Appeals for the Federal Circuit, most recent entry date of Jul. 23, 2010, 5 pages.

"Non-Confidential Brief for Defendant-Appellant" in *Duramed Pharmaceuticals, Inc.* v. *Watson Laboratories, Inc.*, Case No. 10-1331, U.S. Court of Appeals for the Federal Circuit, filed Jun. 28, 2010, 69 pages.

"First Amended Answer, Affirmative Defenses and Counterclaims of Defendants Watson Laboratories, Inc. and Watson Pharmaceuticals, Inc. to Teva Wotnen's Health, Inc.'s Complaint" in *Teva Women's Health, Inc.* v. *Lupin, Ltd. et al.*, Civil Docket Case No. 2:10-CV-00080, U.S. District Court, District of New Jersey (Newark), filed May 28, 2010, 45 pages, including Exhibit A.

Docket Sheet for *Teva Women's Health, Inc.* v. *Mylan Pharmaceuticals, Inc. et al*, Civil Docket Case No. 2:10-CV-01235, U.S. District Court, District of New Jersey (Newark), most recent entry date of Oct. 1, 2010, 9 pages.

Docket Sheet for *Teva Women's Health, Inc.* v. *Lupin, Ltd. et al*, Civil Docket Case No. 2:10-CV-00080, U.S. District Court, District of New Jersey (Newark), most recent entry date of Oct. 15, 2010, 23 pages.

"Exhibit 9 - Redacted" (Part 1 of Expert Report of Patricia J. Sulak, M.D.) to "Redaction to Order on Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Aug. 30, 2010, 50 pages.

"Exhibit 9 - Redacted" (Part 2 of Expert Report of Patricia J. Sulak, M.D.) to "Redaction to Order on Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Aug. 30, 2010, 48 pages.

"Exhibit 10 - Redacted" (Part 1 of Deposition of Patricia J. Sulak, M.D.) to "Redaction to Order on Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Aug. 30, 2010, 101 pages.

"Exhibit 10 - Redacted" (Part 2 of Deposition of Patricia J. Sulak, M.D.) to "Redaction to Order on Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Aug. 30, 2010, 100 pages.

"Exhibit 10 - Redacted" (Part 3 of Deposition of Patricia J. Sulak, M.D.) to "Redaction to Order on Motion to Seal by Teva Women's Health, Inc." in *Teva Women's Health, Inc.* v. *Lupin, Ltd. et al*, Civil Docket Case No. 2:10-CV-00080, U.S. District Court, District of New Jersey (Newark), filed Aug. 30, 2010, 83 pages.

"Notice of Motion for Leave to File First Amended Answer and Counterclaims of Lupin Pharmaceuticals, Inc. and Lupin, Ltd." in *Teva Women's Health, Inc.* v. *Lupin, Ltd. et al*, Civil Docket Case No. 2:10-CV-00080, U.S. District Court, District of New Jersey (Newark), filed Oct. 8, 2010, 18 pages.

Docket Sheet for *Teva Women's Health, Inc.* v. *Mylan Pharmaceuticals, Inc. et al*, Civil Docket Case No. 2:10-CV-01234, U.S. District Court, District of New Jersey (Newark), most recent entry date of October 8, 2010, 13 pages.

Docket Sheet for *Duramed Pharmaceuticals, Inc.* v. *Sandoz Inc.*, Civil Docket Case No. 3:07-CV-05940, U.S. District Court, District of New Jersey (Trenton), most recent entry date of October 15, 2010, 25 pages.

Docket Sheet for *Duramed Pharmaceuticals, Inc.* v. *Watson Laboratories, Inc.*, Case No. 10-1331, U.S. Court of Appeals for the Federal Circuit, most recent entry date of Sep. 2, 2010, 5 pages.

\* cited by examiner

ORAL CONTRACEPTIVES TO PREVENT PREGNANCY AND DIMINISH PREMENSTRUAL SYMPTOMATOLOGY

CROSS-REFERENCE TO RELATED APPLICATIONS

This application is a divisional of U.S. application Ser. No. 10/309,313, filed Dec. 4, 2002, which claims the benefit of U.S. Provisional Application No. 60/335,807, filed Dec. 5, 2001. The disclosures of both of these applications are hereby incorporated herein by reference in their entireties.

BACKGROUND OF THE INVENTION

1. Field of the Invention

This invention relates to oral contraceptives that prevent pregnancy and diminish or eliminate premenstrual symptomatology, including PMS and PMDD, and to a method of preventing pregnancy and diminishing or eliminating premenstrual symptomatology, including PMS and PMDD.

2. Background Art

The human menstrual cycle involves a repetitive sequence of hormonal changes that result in episodic uterine bleeding. Normally, each menstrual cycle has a mean interval of 21 to 35 days, conventionally beginning with the first day of menstrual flow and ending on the day before the next onset of bleeding. Duration of the menstrual flow is usually 2 to 6 days with loss of 20 to 60 ml of blood.

The menstrual cycle is divided into follicular and luteal phases, each corresponding to changes occurring in the ovary. These phases may also be described as proliferative or secretory, corresponding to changes observed in the uterine endometrium. Variations in the length of the cycle are usually due to alterations in the follicular phase, because the luteal phase length remains relatively constant at 12 to 16 days.

During the follicular phase, several primary follicles are recruited for further growth and development. Granulosa cells in primary follicles posses follicle stimulating hormone (FSH) and estradiol receptors. Upon FSH stimulation, granulosa cells produce aromatase. This enzyme converts the androgens androstenedione and testosterone, made in response to luteinizing hormone (LH) by thecal cells, to estrone and estradiol, respectively. Granulosa cells respond to estradiol by undergoing mitosis to increase the number of granulosa cells and estradiol production. By day 7 of the cycle, one enlarging primary follicle is selected by unknown processes to be the follicle that will release the oocyte at ovulation.

The midcycle rise in plasma estradiol stimulates the large midcycle LH surge. This midcycle LH surge triggers resumption of meiosis within the oocyte and luteinization of the granulosa cells within the preovulatory follicle. Immediately before ovulation, the outer follicular wall begins to dissolve and an oocyte is released approximately 24 to 36 hours from the onset of the LH surge.

After ovulation, granulosa cells and the surrounding theca cells enlarge, accumulate lipid, and become transformed into lutein cells. This begins the luteal phase of the menstrual cycle. These cells form a new vascularized structure called the corpus luteum, which secretes estradiol and progesterone. LH maintains the corpus luteum during the luteal phase and, acting via the adenyl cyclase system, stimulates progesterone production. If pregnancy does not occur, lutein cells degenerate, and diminished hormone secretion precedes menstruation. Menstruation is immediately followed by the onset of another menstrual cycle.

Because endometrial proliferation serves to prepare the uterus for an impending pregnancy, manipulation of hormones and of the uterine environment can provide contraception. For example, estrogens are known to decrease FSH secretion by feedback inhibition. Under certain circumstances, estrogens can also inhibit LH secretion, once again by negative feedback. Under normal circumstances, the spike of circulating estrogen found just prior to ovulation induces the surge of gonadotropic hormones that occurs just prior to and results in ovulation. High doses of estrogen immediately post-coitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits LH secretion and blocks ovulation in humans.

The most prevalent form of oral contraception is a pill that combines both an estrogen and a progestin, a so-called combined oral contraceptive preparation.

Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et al., *Contraception* 25:243 (1982)).

In establishing an estrogen-progestin regimen for oral contraceptives, two principal issues must be confronted. First, efficacy must be maintained and second, there must be avoidance of further erosion in the control of endometrial bleeding. In general, even the lowest dose oral contraceptive products commercially available have demonstrated efficacy but the overall instances of bleeding control problems have increased as the doses were reduced, as manifested both in breakthrough bleeding (untimely flow or spotting) or withdrawal amenorrhea during the "pill free" week (expected menses).

During the luteal phase of the menstrual cycle, as many as 75% of women with regular menstrual cycles experience some symptoms of premenstrual syndrome (PMS), a recurring, cyclical disorder involving behavioral, emotional, social and physical symptoms (Steiner et al., *Annu. Rev. Med.* 48:447-455 (1997)). Behavioral, emotional and social symptoms include, but are not limited to, irritability, mood swings, depression, hostility and social withdrawal. Physical symptoms include, but are not limited to, bloating, breast tenderness, myalgia, migraines or headaches and fatigue. True PMS only occurs during the luteal phase of the menstrual cycle, with a symptom-free period during the follicular phase. The etiology of PMS is still unknown.

A subgroup of women with PMS, about 2-9%, exhibit symptoms that are primarily related to a severe mood disorder. In these women, the diagnosis of Premenstrual Dysphoric Disorder (PMDD), which is defined in the Fourth edition of the Diagnostic and Statistical Manual of Mental Disorders (DSM-IV) can be applied. According to the DSM-IV, a woman with PMDD must have at least five premenstrual symptoms during the luteal phase, with at least one of the symptoms being an emotional or "core" symptom. The core symptoms must be irritability, anger, mood swings, tension or depression (and interfere with daily activities), and must be confirmed by a prospective daily rating for at least two cycles. Three to five percent of women with PMS report to have PMDD.

There is also a subgroup of women who experience severe PMS, which accounts for about 20% of the PMS population. These women experience severe emotional symptoms that do not fall under the strict criteria of PMDD as defined in DSM-IV but require medical attention.

Symptoms of PMDD may begin at any age after menarche, but the average age at onset appears to be around 26 years and several researchers found that symptoms, such as estrogen withdrawal symptoms, associated with the premenstrual phase gradually become worse, and perhaps more protracted, over time. It has been suggested that worsening could occur because of the recurring increases and decreases in ovarian hormones. This is supported by data from other cultures: when menstruation is infrequent, premenstrual symptoms are rare. It is also supported by data associating low parity with the risk of PMDD. Low parity yields a greater number of hormonal cycles, and, thus, a woman has more exposure to and withdrawal from massive amounts of progesterone. Further, several studies find lower rates of premenstrual symptoms among users of oral contraceptives, again suggesting that briefer exposure to peaks and troughs of endogenous progesterone is protective against PMDD (Yonkers, K., *J. Clin. Psychiatry* 58 (*Suppl.* 14): 4-13 (1997)).

Suppression of ovulation has been an important rationale for the use of hormonal treatments for PMS. One method of inhibiting ovulation is by using oral contraceptives (OCs). Combination oral contraceptives inhibit ovulation by suppressing gonadotropins, follicle stimulating hormone (FSH) and luteinizing hormone (LH). To date, only two controlled studies of the oral contraceptive treatment of PMS have been published. The results indicate that combination oral contraceptives effectively reduce physical symptoms (especially breast pain and bloating), but the response on the relief of psychological symptoms has been less clear.

Therapeutic interventions for women who meet the criteria for PMDD include selective serotonin reuptake inhibitors (SSRI), tricyclic antidepressants and anxiolytics, as well as the antidepressant alprazolam (XANAX®). These interventions have demonstrated efficacy with minimal side effects. Recent investigations of SSRI have also demonstrated success at low doses.

Antidepressants that are active at serotonin receptors include clomipramine (ANAFRANIL®), fluoxetine (PROZAC®), paroxetine (PAXIL®), sertraline (ZOLOFT®), nefazodone (SERZONE®), fenfluramine (PONDIMIN®) and venlafaxine (EFFEXOR®).

The only approved product today for the treatment of PMDD is the SSRI fluoxetine hydrochloride (SARAFEM®). The effectiveness of fluoxetine for the treatment of PMDD was established in four randomized, placebo-controlled trials. Fluoxetine at a daily dose of either 20 mg or 60 mg proved to be superior to placebo in reducing symptoms (Steiner et al., *New Engl. J. Med.* 332:1529-34 (1995)). However, the combination of oral contraceptive and fluoxetine was not examined, as women who were taking oral contraceptives were excluded from the trial.

It is the object of the present invention to provide estrogen-progestin combinations and/or regimens for oral contraceptive use, including estrogen-progestin combinations and/or regimens that contain an antidepressant, to concurrently diminish or eliminate premenstrual symptoms (PMS) including PMDD. Two regimens are proposed, the so-called 28-day regimen and the 91-day regimen. The 28-day regimen will allow women the option of maintaining the customary 13 menstrual cycles per year while diminishing or alleviating premenstrual symptoms (PMS) including PMDD. The 91-day regimen will allow women the option of maintaining only 4 menstrual cycles per year while diminishing or alleviating premenstrual symptoms (PMS) including PMDD. Thus, the 91-day regimen enhances compliance by involving fewer stop/start transitions per year and also results in less blood loss, and hypothetically, will diminish premenstrual symptoms, including PMDD. Having fewer menstrual intervals can also enhance lifestyles and convenience. This and other objects of the invention will become apparent to those skilled in the art from the following detailed description.

BRIEF SUMMARY OF THE INVENTION

This invention relates to female oral contraceptives that will prevent pregnancy and treat PMS including PMDD. This invention further relates to a method of preventing pregnancy and treating PMS including PMDD, by avoiding complete withdrawal of estrogen at the end of the treatment period, or between treatment periods, by administering oral contraceptives. Premenstrual symptoms are rare when menstruation is infrequent. Further, users of oral contraceptives have lower rates of premenstrual symptoms, again suggesting that briefer exposure to peaks and troughs of endogenous progesterone is protective against PMDD. More particularly, the invention relates to a method of preventing pregnancy, which involves administering one of two combination oral contraceptive regimens. Additionally, the invention relates to a method of preventing pregnancy, which involves administering one of two combination oral contraceptive regimens that contain an antidepressant.

DETAILED DESCRIPTION OF THE INVENTION

The invention relates to oral contraceptives that will prevent pregnancy and diminish or eliminate PMS including PMDD. Methods of using these oral contraceptives to prevent pregnancy and diminish or eliminate PMS including PMDD are also provided. More particularly, the methods involve administering one of several combination oral contraceptive regimens. Importantly, these regimens do not contain pill-free or placebo intervals.

One embodiment of the invention is the so-called twenty-eight day regimen that allows women the option of maintaining 13 menstrual cycles per year. In accordance with the present invention, a women in need of contraception and treatment of PMS including PMDD, is administered a combined dosage form of estrogen and progestin, preferably monophasicly, for 21 to 26 consecutive days, preferably about 22-25 days, followed by administration of low-dose estrogen for 2 to 10 days, preferably about 3-7 days, more preferably about 2-7 days, in which the daily amounts of estrogen and progestin are equivalent to about 5-50 μg of ethinyl estradiol and about 0.025 to 10 mg, preferably about 0.05 to 1.5 mg, of levonorgestrel, respectively.

In a preferred embodiment, women will be administered an oral contraceptive on days 1 through 21 of the menstrual cycle containing 150 μg levonorgestrel and 30 μg ethinyl estradiol, followed by a dosage form on days 22-28 of the cycle, which contains 30 μg ethinyl estradiol. A typical administration schedule is illustrated in Table 1. Thus, in a 28-day regimen schedule, there are about 13 treatment and menstrual cycles per year.

TABLE 1

Administration schedule for a 28-day regimen

| Days | Hormone | Antidepressant |
|---|---|---|
| 1-21 | 150 µg levonorgestrel and 30 µg ethinyl estradiol | none |
| 22-28 | 30 µg ethinyl estradiol | none |

In another embodiment of the invention, a women in need of contraception and treatment of PMS including PMDD, is administered a combined dosage form of estrogen and progestin, preferably monophasicly, for 21 to 26 consecutive days, preferably about 22-25 days, followed by administration of low-dose estrogen for 2 to 10 days, preferably about 3-7 days, more preferably about 2-7 days, in combination with the antidepressant fluoxetine hydrochloride, in which the daily amounts of estrogen and progestin are equivalent to about 5-50 µg of ethinyl estradiol and about 0.025 to 10 mg, preferably about 0.05 to 1.5 mg, of levonorgestrel, respectively, and the fluoxetine hydrochloride is in an amount of about 5-120 mg. Oral contraceptives with initial doses of fluoxetine at either 5 mg or 10 mg/day can be started to avoid any activating side effects that may lead to noncompliance. The dose can then be increased as needed. Fluoxetine can also be given intermittently during the late luteal phase, which is typically 1-2 weeks before menses. In addition, a one-time or once-weekly dose of about 90 mg of fluoxetine can be administered.

In a preferred embodiment, women will be administered an oral contraceptive on days 1 through 21 of the menstrual cycle containing 150 µg levonorgestrel and 30 µg ethinyl estradiol, followed by a dosage form on days 22-28 of the cycle, which contains 20 mg fluoxetine hydrochloride and 30 µg ethinyl estradiol. A typical administration schedule is illustrated in Table 2. Thus, in a 28-day regimen schedule, there are about 13 treatment and menstrual cycles per year.

TABLE 2

Administration schedule for a 28-day regimen with an antidepressant

| Days | Hormone | Antidepressant |
|---|---|---|
| 1-21 | 150 µg levonorgestrel and 30 µg ethinyl estradiol | none |
| 22-28 | 30 µg ethinyl estradiol | 20 mg fluoxetine hydrochloride daily OR a one-time dose of 90 mg fluoxetine hydrochloride OR a once-weekly dose of 90 mg fluoxetine hydrochloride |

An additional embodiment of the invention is a long-term regimen that allows women the option of limiting their menstrual periods to about four times per year. In accordance with the present invention, a women in need of contraception and treatment of PMS including PMDD, is administered a combined dosage form of estrogen and progestin, preferably monophasicly, for 60 to 110 consecutive days, preferably about 81 to 89 days, followed by administration of estrogen for 2 to 10 days, preferably about 5 to 8 days, in which the daily amounts of estrogen and progestin are equivalent to about 5-50 µg of ethinyl estradiol and about 0.025 to 10 mg, preferably about 0.05 to 1.5 mg, of levonorgestrel, respectively.

In a preferred embodiment, the 91-day regimen, women will be administered an oral contraceptive on days 1 through 84 of the menstrual cycle containing 150 µg levonorgestrel and 30 µg ethinyl estradiol, followed by a dosage form on days 85-91 of the cycle, which contains 30 µg ethinyl estradiol. A typical administration schedule is illustrated in Table 3. Thus, in a 91-day regimen, there are only four treatment and menstrual cycles per year.

TABLE 3

Administration schedule for a 91-day regimen

| Days | Hormone | Antidepressant |
|---|---|---|
| 1-84 | 150 µg levonorgestrel and 30 µg ethinyl estradiol | none |
| 85-91 | 30 µg ethinyl estradiol | none |

In an additional embodiment of the invention, a women in need of contraception and treatment of PMS including PMDD, is administered a combined dosage form of estrogen and progestin, preferably monophasicly, for 60 to 110 consecutive days, preferably about 81 to 89 days, followed by administration of low-dose estrogen and fluoxetine hydrochloride for 2 to 10 days, preferably about 5 to 8 days, in which the daily amounts of estrogen and progestin are equivalent to about 5-50 µg of ethinyl estradiol and about 0.025 to 10 mg, preferably about 0.05 to 1.5 mg, of levonorgestrel, respectively, and the fluoxetine hydrochloride is in an amount of about 5-120 mg. Oral contraceptives with initial doses of fluoxetine at either 5 mg or 10 mg/day can be started to avoid any activating side effects that may lead to noncompliance. The dose can then be increased as needed. Fluoxetine can also be given intermittently during the late luteal phase, which is typically 1-2 weeks before menses. In addition, a one-time or once-weekly dose of about 90 mg of fluoxetine can be administered.

In a preferred embodiment, women will be administered an oral contraceptive on days 1 through 84 of the menstrual cycle containing 150 µg levonorgestrel and 30 µg ethinyl estradiol, followed by a dosage form on days 85-91 of the cycle, which contains 30 µg ethinyl estradiol and 20 mg fluoxetine hydrochloride. A typical administration schedule is illustrated in Table 4. Thus, in a 91-day regimen, there are only four treatment and menstrual cycles per year.

TABLE 4

Administration schedule for a 91-day regimen with an antidepressant

| Days | Hormone | Antidepressant |
|---|---|---|
| 1-84 | 150 µg levonorgestrel and 30 µg ethinyl estradiol | none |
| 85-91 | 30 µg ethinyl estradiol | 20 mg fluoxetine hydrochloride daily OR a one-time dose of 90 mg fluoxetine hydrochloride OR a once-weekly dose of 90 mg fluoxetine hydrochloride |

The estrogens which may be employed as a component in the regimens of this invention may be any of those conventionally available. Typically, the estrogen may be selected from the group comprising synthetic and natural estrogens, including steroidal and nonsteroidal estrogens. The synthetic estrogens may be selected from, for example, ethinyl estradiol, ethynodiol diacetate, mestranol and quinestranol. Particularly of interest are 17α-ethinyl estradiol and esters and ethers thereof. The preferred estrogen is 17α-ethinyl estradiol. The natural estrogens may include, for example, conjugated equine estrogens, esterified estrogens, 17β-estradiol, estradiol valerate, estrone, piperazine estrone sulphate, estriol, estriol succinate and polyestrol phosphate.

The progestin component may be any progestationally active compound. Thus, the progestin may be selected from progesterone and its derivatives such as, for example, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, dl-norgestrel, d-17α-acetoxy-13β-ethyl-17α-ethinyl-gon-4-en-3-one oxime, cyproterone acetate, gestodene, desogestrel and norgestimate. The preferred progestin is levonorgestrel.

The weight ratio of the active ingredients, e.g., ethinyl estradiol and levonorgestrel, is at least 1:45 and preferably at least 1:50. The preferable amount of ethinyl estradiol is about 10-50 μg and the preferable amount of levonorgestrel is about 0.15-1.5 mg. Other estrogens vary in potency from ethinyl estradiol. For example, 30 μg of ethinyl estradiol is roughly equivalent to 60 μg of mestranol or 2 g of 17β-estradiol. Likewise, other progestins vary in potency from levonorgestrel. Thus, 1 mg of levonorgestrel is roughly equivalent to about 3.5 mg of norethindrone acetate, or 1 mg of desogestrel and 3-ketodesogestrel or about 0.7 mg of gestodene. The values given above are for ethinyl estradiol and levonorgestrel and if a different estrogen or progestin is employed, an adjustment in the amount based on the relative potency should be made. The correlations in potency between the various estrogens and progestins are known. See for example European Patent Application No. 0 253 607, which is hereby incorporated in its entirety by reference hereto.

The preferred antidepressant is fluoxetine hydrochloride although other antidepressants can be employed. For example, the antidepressants alprazolam (XANAX®), clomipramine (ANAFRANIL®), paroxetine (PAXIL®), sertraline (ZOLOFT®), nefazodone (SERZONE®), fenfluramine (PONDIMIN®) and venlafaxine (EFFEXOR®) can also be used. The daily amounts of these antidepressants can vary, depending on the antidepressant used, from 0.75 to 2 mg, 10 to 20 mg or 50 to 100 mg.

Each of the described regimens will prevent pregnancy and additionally diminish or eliminate debilitating premenstrual symptomatology.

Other useable estrogens include the esters of estradiol, estrone and ethinyl estradiol such as the acetate, sulfate, valerate or benzoate, conjugated equine estrogens, agnostic antiestrogens, and selective estrogen receptor modulators. The formulations of the invention may be administered orally, preferably in tablet form, parenterally, sublingually, transdermally, intravaginally, intranasally or buccally. The method of administration depends on the types of estrogens and progestins used in the formulation, as well as the amounts per unit dosage. Most estrogens are orally active and that route of administration is therefore preferred. Methods for transdermal administration including the associated methods for manufacturing such systems are well known in the art. In this connection, reference may be had to U.S. Pat. Nos. 4,752,478, 4,685,911, 4,438,139 and 4,291,014, which are hereby incorporated in their entirety by reference hereto.

Pharmaceutical formulations or preparations containing the formulations of the invention and a suitable carrier can be solid dosage forms which includes tablets, dragees, capsules, cachets, pellets, pills, powders or granules; topical dosage forms which include solutions, powders, fluid emulsions, fluid suspensions, semi-solids, ointments, pastes, creams, gels or jellies, foams and controlled release depot entities; transdermals, vaginal rings, buccal formulations; and parenteral dosage forms which includes solutions, suspensions, emulsions or dry powder comprising an effective amount of estrogen, progestin and antidepressant as taught in this invention.

It is known in the art that active ingredients can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. (1979); "Goodman & Gilman's The Pharmaceutical Basis of Therapeutics", 6th Edition, MacMillan Publishing Co., New York (1980), or Remington's Pharmaceutical Sciences, Osol, A., ed., Mack Publishing Company, Easton, Pa. (1980) can be consulted.

Generally speaking, the formulations are prepared according to conventionally known procedures in accordance with the method of administration. Thus, the active ingredients are prepared according to known methods in a pharmaceutically acceptable form for administration. These ingredients, in their required quantities are combined with the appropriate pharmaceutical carriers such as additives, vehicles and/or flavor ameliorating substances. These substances may be referred to as diluents, binders and lubricants. Gums, starches and sugars are also common terms. Typical of these types of substances or excipients are pharmaceutical grades of mannitol, lactose starch, magnesium stearate, sodium saccharin, talcum, cellulose, glucose, sucrose, magnesium carbonate and the like. The active ingredient(s) may comprise from about 0.01% by weight to about 99.99% by weight of the total formulation and the remainder comprises the pharmaceutically acceptable carrier. The percentage of active ingredient(s) may vary according to the delivery system or method of administration and is chosen in accordance with conventional methods known in the art.

In the oral form of the formulation, the contraceptive preparations are preferably produced in the form of a kit or package, with the daily dosages arranged for proper sequential administration. Thus, in another aspect, the present invention also provides a pharmaceutical package which contains combination-type contraceptives in multiple dosage units in a synchronized, fixed sequence, wherein the sequence or arrangement of the dosage units corresponds to the stages of daily administration.

For example, the pharmaceutical formulations may be provided in kit form containing for the 28-day regimen at least about 18, and preferably at least about 21 tablets, and up to 26 tablets, intended for ingestion on successive days. Preferably administration is daily for at least 21 days using tablets containing both the estrogen and the progestin and then for at least 7 days using tablets containing only estrogen. In another preferred embodiment, administration is daily for at least 21 days using tablets containing both the estrogen and the progestin and then for at least 7 days using tablets containing both estrogen and an antidepressant, e.g., fluoxetine hydrochloride. For the long-term regimen, the pharmaceutical formulation may be provided in kit form containing at least about 60, and preferably at least about 81 to 89 tablets, and up to 110 tablets, intended for ingestion on successive days. Preferably administration is daily for at least 84 days using tablets containing both the estrogen and the progestin and then for at least 7 days using tablets with only estrogen. In another preferred embodiment, administration is daily for at least 84 days using tablets containing both the estrogen and the progestin and then for at least 7 days using tablets with both estrogen and an antidepressant, e.g., fluoxetine hydrochloride.

Efficacy of the 28-day and 91-day regimens on premenstrual symptomatology are measured by psychometric scales that include self-administered Visual Analogue Scales (VAS) and a prospective daily symptoms chart or diary to evaluate psychological and somatic symptoms. Total score of the psychological and somatic symptoms is computed. The VAS measures tension, irritability, dysphoria, sleeping and eating patterns, headache, bloating, pain and breast tenderness and weight gain symptoms.

In order to further illustrate the present invention, specific examples are set forth below. It will be appreciated, however, that these examples are illustrative only and are not intended to limit the scope of the invention.

EXAMPLES

Example 1

Multicenter Randomized Phase III Clinical Trial to Evaluate Two Continuous Oral Contraceptive Regimens in Women Diagnosed with Premenstrual Syndrome (PMS) and Premenstrual Dysphoric Disorder (PMDD)

Clinical Design and Summary

In a multicenter, randomized, clinical trial the efficacy and safety of three combination oral contraceptives regimens in the prevention of pregnancy in sexually active women, ages 18 through 40 years, will be evaluated. Patients will be randomized in a 1:1:1 fashion to one of the following regimens:

Levonorgestrel 150 µg/ethinyl estradiol (EE) 30 µg administered once daily for 84 days as a combination oral tablet followed by ethinyl estradiol 30 µg administered once daily for 7 days (DP3-84/30);

Levonorgestrel 150 µg/ethinyl estradiol 30 µg administered once daily for 84 days as a combination oral tablet followed by ethinyl estradiol 10 µg administered once daily for 7 days (DP3-84/10); or Levonorgestrel 150 µg/ethinyl estradiol 30 µg administered once daily for 25 days as a combination oral tablet followed by ethinyl estradiol 30 µg administered once daily for 3 days (DP3-25/30).

Patients randomized to either DP3-84/30 or DP3-84/10 will receive 4 cycles of study drug. Patients randomized to DP3-25/30 will receive 13 cycles of study drug. All patients will receive approximately 1 year of therapy.

The study coordinator or designated personnel will register the patient. Patients will be randomly assigned to one of the treatment regimens. The treatment group assignment will not be revealed to the patient prior to signing of the informed consent.

All patients, regardless of randomization, will initiate study OC therapy on the first Sunday following the beginning of their menstrual period ("Sunday starters") and will remain as Sunday starters throughout the study. Each of the dose packs will be dispensed with an abbreviated patient information sheet and a more detailed patient package insert (PPI).

All patients will complete and download information entered into an electronic diary. Assessments will include study drug compliance, use of additional forms of contraception, bleeding patterns, weight, assessment of the incidence and severity of menstrual related symptoms and medication taken to relieve these symptoms. Information will be self-recorded on the electronic diary via a series of pre-programmed questions.

Two hundred (200) patients in each treatment arm are targeted to complete the study. Pregnancy rate will be calculated using data from those patients age 18 to 35. Patients age 36 through 40 will also be enrolled.

Patient Eligibility

Inclusion Criteria

Patients must meet the following criteria to be included in the study:

1. Sexually active adult females (age 18 through 40), of child bearing potential, in a heterosexual relationship, at risk for pregnancy, who are in good health and who
   have a history of OC use for an interval of at least three successive cycles with regular withdrawal bleeding (bleeding during the pill-free interval or during the first three days of the subsequent cycle) prior to enrollment (Continuous Users)
   OR
   have no prior history OC use (Fresh-Starts)
   OR
   have no history of OC use in the 6 months prior to enrollment (Prior Users)
2. Negative urine pregnancy test.
3. Signed informed consent.
4. Agree to use study oral contraceptive therapy as their primary birth control method (BCM).

Exclusion Criteria:

Patients will be excluded from the study if any of the following criteria are met:

1. History of hypersensitivity to estrogen or progestin components of OCs.
2. History of alcohol or drug abuse which, in the opinion of the investigator, makes the patient unfit for participation in the study.
3. Active smoker age>34 years.
4. Chronic use of any medication that may interfere with the efficacy of oral contraceptives.
5. History of being HIV or Hepatitis C positive.
6. History of persistent noncompliance with any chronic medication.
7. History of having received injectable hormone therapy (e.g., Depo-Provera<(Pharmacia and Upjohn)) within the 10 months prior to enrollment or having a progestin-releasing intrauterine device (IUD) in place within 3 months prior to enrollment or has had a contraceptive implant removed within one month prior to enrollment or has received any other form of hormonal contraception within 3 months prior to enrollment.
8. Routine concomitant use of additional forms of contraception (IUD, diaphragm, contraceptive sponge) with the exception of condoms.
9. Patients who have had recent surgical or medical abortion, miscarriage, or vaginal or cesarean delivery must have had at least two normal menstrual cycles prior to enrollment.
10. History of abnormal bleeding (breakthrough or withdrawal bleeding that lasts≧10 consecutive days or excessive spotting that lasts≧10 consecutive days) while on conventional oral contraceptives.

11. History of thromboembolic disorder, vascular disease, cerebral vascular or coronary artery disease.
12. Uncontrolled or untreated hypertension (systolic BP≧140 mmHg and diastolic BP≧90 mmHg on more than two occasions).
13. Known or suspected carcinoma of the breast, endometrial carcinoma or known or suspected estrogen dependent neoplasia.
14. Undiagnosed abnormal genital bleeding.
15. History of hepatic adenomas or carcinomas.
16. History of cholestatic jaundice of pregnancy or jaundice with prior OC use.
17. Known or suspected pregnancy or currently breastfeeding.
18. Hyperlipidemia requiring active treatment with antihyperlipidemic agents.
19. History of diabetes mellitus, glucose intolerance or gestational diabetes.
20. History of abnormal laboratory value at screening
21. Any clinically significant abnormal finding or condition on history, screening, physical exam, pelvic exam or any laboratory finding which contraindicates the use of oral contraceptives.
22. Has participated in any clinical investigation within the 30 days prior to enrollment.
23. Has donated or had a loss of more than 500 cc of blood within the 30 days prior to enrollment.

Treatment Regimen

Description of Study Medication

DP3-84/30

All tablets in the DP3-84/30 regimen; 84 tablets each containing 150 μg levonorgestrel/30 μg EE and 7 tablets each containing 30 μg of EE will be white unembossed tablets. One combination tablet will be taken each day for 84 days followed by 7 days of EE tablets in 91-day cycles repeated consecutively for approximately one year (4 cycles). Each DP3-84/30 dose kit will be packaged in a 3-part fold-out white blister card pack where each of the first two blister packs has 28 active tablets each and the third blister pack has 28 active tablets and 7 ethinyl estradiol tablets (35 tablets total) for each 91-day cycle.

Each blister card pack will be sealed into a foil pouch, which will be labeled with a patient-specific label. Each foil pouch will contain an oxygen absorber. At each clinic visit one foil pouch, a patient information sheet, a PPI and a child resistant pouch will be dispensed.

DP3-84/10

All tablets in the DP3-84/10 regimen; 84 tablets each containing 150-μg levonorgestrel/30-μg EE and 7 tablets each containing 10 μg of EE will be white unembossed tablets. One combination tablet will be taken each day for 84 days followed by 7 days of EE tablets in 91-day cycles repeated consecutively for approximately one year (4 cycles). Each DP3-84/10 dose kit will be packaged in a 3-part fold-out white blister card pack where each of the first two blister packs has 28 active tablets each and the third blister pack has 28 active tablets and 7 ethinyl estradiol tablets (35 tablets total) for each 91-day cycle.

Each blister card pack will be sealed into a foil pouch, which will be labeled with a patient-specific label. Each foil pouch will contain an oxygen absorber. At each clinic visit one foil pouch, a patient information sheet, a PPI and a child resistant pouch will be dispensed.

DP3-25/30

All tablets in the DP3-25/30 regimen; 25 tablets each containing 150-μg levonorgestrel/30-μg EE and 3 tablets each containing 30 μg of EE will be white unembossed tablets. One combination tablet will be taken each day for 25 days followed by 3 days of EE tablets in 28-day cycles repeated consecutively for approximately one year (13 cycles). Each DP3-25/30 blister card will have 25 active tablets followed by 3 ethinyl estradiol tablets (28 tablets total) for each 28-day cycle.

Each blister card will be sealed into a foil pouch, which will be labeled with a patient-specific label. Each foil pouch will contain an oxygen absorber. At clinic visits one through three, 3 foil pouches, a patient information sheet, a PPI and a child resistant pouch will be dispensed. At clinic visit four, 4 foil pouches, a patient information sheet, a PPI and a child resistant pouch will be dispensed.

All patients, regardless of randomization, will be instructed to initiate OC therapy on the first Sunday following the beginning of their menstrual period ("Sunday starters"). Patients will be instructed to take their study medication at the same time each day. Day 1 of the study will be defined as the first day of study medication.

Administration

Designated personnel will dispense all study drugs. All study medications must be kept in a secured area at temperature ranging from approximately 15-25° C. (59-77° F.). All patients will be instructed to take one tablet per day at approximately the same time each day. All patients will be "Sunday starters"; that is all patients will begin study drug therapy on the first Sunday following the start of their previous menstrual cycle or completion of prior oral contraceptive regimens. All patients enrolled in the study will maintain Sunday starts for each successive cycle.

The end-of-study evaluation will take place 1 week following completion of withdrawal menses following the last cycle of study OC therapy. At the clinic visit during which patients receive the final supply of study medication, they will be counseled to use an alternative method of birth control during the interval between when they have finished study medication until they have completed the final study visit.

Patients randomized to DP3-84/30 or DP3-84/10 will receive a 13-week supply (single cycle) of study drug at each clinic visit during Weeks 13, 26 and 39. Patients randomized to DP3-25/30 will receive a 12-week supply (three-cycles) of study drug at the initiation of the study and at clinic visits during Weeks 12 and 24. During the clinic visit at Week 36 patients randomized to DP3-25/30 will receive 16-week supply (four cycles) of study medication.

TABLE 5

Examinations/Tests
Study Schedule

| Parameter | Screening | Visit 1 | Visits 2-4[a] | Completion of Therapy |
|---|---|---|---|---|
| Informed consent | X | | | |
| Medical and contraceptive history | X | | | |
| Physical exam including pelvic exam | X | | | X |
| Weight, vital signs | X | X | X | X |
| Pap smear | X | | | X |
| Randomization | | X | | |
| Clinical laboratory tests[b] | X | | | X |
| Urine pregnancy test[c] | X | X | X | X |
| Study drug distribution[d] | | X | X | |
| Electronic diary distribution | | X | | |

TABLE 5-continued

Examinations/Tests
Study Schedule

| Parameter | Screening | Visit 1 | Visits 2-4[a] | Completion of Therapy |
|---|---|---|---|---|
| Study drug compliance measurement | | | X | X |
| Adverse event recording | | | X | X |

[a] Patients randomized to DP3-84/30 or DP3-84/10 will be seen at Weeks 13, 26 and 39. Patients randomized to DP3-25/30 will be seen at Weeks 12, 24, and 40.
[b] Clinical laboratory tests include CBC, serum chemistry, lipid profile, urinalysis
[c] Repeated on Visit 1 if the screening was completed more than 2 weeks prior to enrollment
[d] For patients randomized to DP3 25/30, three (3) cycle supply will be dispensed at Weeks 12 and 24; a four (4) cycle supply will be dispensed at Week 40.

Study Procedures by Visit

Screening and Enrollment

Patients will sign informed consent. Prior to enrollment, within four weeks prior to initiation of study therapy, all patients will undergo a screening evaluation that will include prior medical and contraceptive history, smoking history, physical examination including pelvic exam and Pap smear, vital signs and weight, and clinical laboratory tests including complete blood count (CBC), serum chemistry, lipid profile, urinalysis, and urine pregnancy test.

All clinical laboratory evaluations (blood and urine) will be tested by a central laboratory. All investigators will be provided with a laboratory manual that outlines sampling and shipping procedures.

If the screening evaluation is completed more than two weeks prior to the initiation of study therapy, the urine pregnancy test must be repeated at Visit 1. Patients with a report of an abnormality on Pap smear will be disqualified for enrollment unless investigator decides the results are not clinically significant and will not interfere with conduct of the study. Investigator's decision must be documented. Patients who have had a normal Pap smear within the three months prior to enrollment in the study will not be required to have the test repeated. A copy of the results must be available in the patient's medical record. Any patient with a report of insufficient cells must have the test repeated and documented as normal prior to enrollment. Patients will then be enrolled in the study.

Visit 1

Visit 1 will take place during the final week of the menstrual cycle prior to beginning study therapy (i.e., during menses for those patients not taking oral contraceptives or during Week 4 for those patients taking oral contraceptives). During Visit 1 patients will be randomized to one of the following treatment groups:

DP3-84/30; levonorgestrel 150 μg/EE 30 μg for 84 days+ EE 30 μg for 7 days
OR
DP3-84/10; levonorgestrel 150 μg/EE 30 μg for 84 days+ EE 10 μg for 7 days
OR
DP3-25/3; levonorgestrel 150 μg/EE 30 μg for 25 days+EE 30 μg for 3 days The treatment regimen assignment will be ascertained by randomization via Interactive Voice Response System (IVRS). The treatment group assignment will not be revealed to the patient prior to signing of the informed consent.

A urine pregnancy test will be re-administered to those women who were screened more than two weeks prior to Visit 1. Study medication will be dispensed with patient instructions. An electronic diary will be given to each patient. Each patient will be trained regarding the use and care of the electronic diary. Patients will be instructed to take each dose of study medication and to complete all diary entries at approximately the same time each day.

Visits 2-4

All visits should take place within seven days prior to completion of study medication for that cycle. Any visit that takes place prior to the final week of the cycle will be recorded as a protocol deviation. Any visit that takes place following the final week of the cycle resulting in a lapse in study medication intake will be recorded as a protocol violation and will result in the patient being withdrawn from the study. Any visit that takes place following the final week of the cycle but does not result in a lapse in study medication (e.g., the patient received an emergency supply of study medication) will be recorded as a protocol deviation.

Patients randomized to either DP3-84/30 or DP3-84/10 will be seen at Weeks 13, 26 and 39. Patients randomized to DP3-25/30 will be seen at Weeks 12, 24 and 36. During these visits, patients will be queried regarding adverse events, concomitant medications, change in smoking history, and compliance. Vital signs and weight will be recorded. A urine pregnancy test will be conducted. Used study medication will be returned and counted by the study pharmacist or designated personnel.

Completion of Therapy

The end-of-study evaluation will take place 1 week following completion of last cycle of the study drug. Patients will be counseled to use birth control during the interval between when they have finished study medication until they have completed the final study visit. Patients will undergo physical exam, including pelvic exam and pap smear. Vital signs and weight will be recorded. Blood and urine samples for clinical laboratory tests including CBC, serum chemistry, lipid profile, urinalysis and urine pregnancy test will be obtained. Used study medication cards will be returned and counted by the study pharmacist or designated personnel. Patients will be queried regarding adverse events, concomitant medications, change in smoking history and compliance. The electronic diary will be returned.

Post-Study Visit

After study completion/withdrawal, patients will be followed via a phone call for occurrence of pregnancy and until the menstrual cycle returns to normal. The patient based on the cycle pattern prior to the study entry will determine return to normal menstrual cycle. The minimum period of follow up will be 3 months. Patients who decide to use a contraceptive method that regulates/alters menstrual cycle after study completion/withdrawal will be followed for 3 months via a phone call.

Only those patients who have an on-going serious adverse event that has not resolved or those who become pregnant during the course of the study will be followed via clinic visits after completion of the study. Patients with on-going serious adverse events will be followed until the event has been satisfactory managed or resolved. Patients who are pregnant will be followed for eight weeks following delivery or termination of the pregnancy. Infants' health assessment will be followed for eight weeks following delivery. This follow-up may be in the form of a written report from a family physician, obstetrician or pediatrician. All serious adverse events that occur in the three months following discontinuation of therapy will be reported. SAEs that occur at any time after study completion/discontinuation will be reported if investigator determines it is drug-related.

Early Termination

Any patient who withdraws or is withdrawn from the study must return the investigational medication and electronic diary and will be required to complete all procedures for the final visit. All patients will be followed via a phone call for 3 months for the occurrence of pregnancy and until the menstrual cycle return to normal. All patients will be followed via a phone call for three months for the occurrence of serious adverse events.

Examinations and Procedures

Physical Exam, Medical and Gynecologic History

A complete physical and gynecologic exam, including PAP smear, will be performed at screening and at the completion of therapy or upon early withdrawal from the study. Any patient with an abnormal Pap smear will be disqualified for enrollment unless investigator decides the results are not clinically significant and will not interfere with conduct of the study. The Investigator's decision must be documented. Patients who have had a Pap smear reported as within normal limits within the three months prior to enrollment in the study will not be required to have the test repeated. A copy of the results must be available in the patient's medical record. Any patient with a report of insufficient cells must have the test repeated and documented by the investigator as within normal limits prior to enrollment.

Laboratory Safety Tests

Clinical laboratory tests will be performed at screening and at the completion of therapy or upon early withdrawal. All clinical laboratory tests will be done at one central laboratory. Laboratory tests will include CBC, serum chemistry, lipid profile, urinalysis, and urine pregnancy test. In addition, urine pregnancy tests will be conducted at every clinic visit and at the completion of therapy or upon early withdrawal from the study. All urine pregnancy tests will be performed using the Sure Step® Pregnancy Test kit (Applied Biotech, Inc.).

Pregnancy

All patients will be followed for the occurrence of pregnancy for three months following completion of the study. This follow-up may be in the form of a telephone call. All pregnancies that occur during the course of the study or in the three months following completion of the study will be dated using ultrasound to establish the gestational age of the fetus. Patients who become pregnant during the course of the study due to method failure will be followed for eight weeks following delivery or termination of the pregnancy. Infants' health assessment will be followed for eight weeks following delivery. This follow-up may in the form of a documented telephone conversation with associated pediatrician or written report from the associated pediatrician.

Electronic Diaries

Patients will be asked to complete electronic diaries. The diary will be programmed to ask specific questions related to the study compliance, bleeding pattern and occurrence of symptoms that are commonly associated with the hormone fluctuation during the menstrual cycle. The questions will address dosage, compliance, bleeding pattern and hormone-related symptoms either on the scale from 0-3 or using 10 cm Visual Analogue Scale (VAS).

Hand-held data acquisition devices will be used to collect patient responses. The electronic diary will provide patients with a menu-driven, graphical interface to enter diary information (as well as objective data) using a hand-held stylus. Data entry will be electronic and key fields must be completed properly before allowing patient to finish the report. Each report will be downloaded by dial-up network connection.

The electronic diary will incorporate an alarm to remind the patient when to complete their reports. Alarm times will be set by the site and can be specific to the patient preference. The patient will be instructed to complete a diary on a daily basis. Retrospective data entry will not be allowed; reports cannot be completed for previous days. Once each question is completed the patient will confirm the response and will not be permitted to return to that question for modification.

Information on the hormone-related symptoms to be collected is from the Calendar of Premenstrual Experiences (COPE) and Diagnostic and Statistical Manual of Mental Disorders Forth Edition (DSM-IV).

The validity and reliability of the COPE instrument was assessed by Mortola, et al., *Obstet. Gynecol.* 89:179-83 (1990), who administered it throughout two consecutive ovulatory cycles to 36 rigidly screened women with PMS and to 18 controls. The validity of the visual analogue scales applied to the psychological symptoms associated with the PMDD has been previously documented.

Treatment Modifications Based on Toxicity

No significant toxicity is expected from the study medication. However, if the patient develops any symptoms or any abnormal laboratory parameter attributed to the drug, which are considered by the patient and/or physician to be of unacceptable severity, then the study medication should be discontinued.

Concomitant Medications

Patients will be queried regarding concomitant medication use at monthly phone calls and quarterly clinic visits. All concomitant medication use (both prescription and over-the-counter (OTC), including herbal medications and nutritional supplements) must be reported during the study, and recorded on the patient's Case Report Form (CRF).

Patients who require the initiation of chronic therapy with drugs that are known to interact with OCs will be withdrawn from the study. Patients who require intermittent therapy with drugs known to interact with OCs (e.g. antibiotic therapy) will remain in the study and will receive counseling regarding the need for additional contraceptive protection during the entire cycle. Patients will be provided with the list of medications that are know to interact with OC and will be instructed to notify study coordinator as soon as medication is prescribed to receive proper counseling. Notification and counseling can be conducted via the phone and must be documented in the patient's CRF. Those cycles in which drugs known to interact with OC therapy are taken will not be used in the calculation of the pregnancy rate.

The use of emergency contraceptive pills ("morning after pills") is prohibited in the study. Data from any patient who utilizes contraceptive pills others than those provided for the study will not be included in the calculation of the pregnancy rate for that cycle.

Adverse Event Reporting

An Adverse Event (AE) is any reaction, side effect, or other undesirable event that occurs in conjunction with the use of a drug, biological product or diagnostic agent in humans, whether or not the event is considered drug related.

A serious adverse event (SAE) is one that meets any one of the following criteria:

Fatal or life threatening

Requires or prolongs inpatient hospitalization

Results in persistent or significant disability/incapacity

Congenital anomaly

The term "life threatening" in the definition of "serious" refers to an event in which the patient was at risk of death at the time of the event; it does not refer to an event that hypothetically might have caused death if it were more severe. Medical and scientific judgment should be exercised in deciding whether an important medical event is serious. Although the event may not be immediately life threatening, fatal, or result in hospitalization, it should be considered serious when it jeopardizes the patient, or requires an intervention to prevent a serious outcome as defined above.

The AE reporting period for this study begins at the Enrollment Visit and ends at the final clinic visit. The SAE reporting period will continue for 3 month after the final clinic visit. All SAEs will be followed through resolution or until investigator assesses the SAE as chronic or stable.

A preexisting condition (i.e., a disorder present before the AE reporting period started and noted on the pretreatment medical history/physical form) should not be reported as an AE unless the condition worsens or episodes increase in frequency during the AE reporting period.

During the study AEs will be recorded through monthly phone calls and quarterly clinic visits. A call-in number will be provided to the patients who wish to report an adverse event between the scheduled phone calls and clinic visits.

Example 2

Multicenter Randomized Phase III Clinical Trial to Evaluate Two Continuous Oral Contraceptive Regimens in Combination with Fluoxetine Hydrochloride in Women Diagnosed with Premenstrual Syndrome (PMS) and Premenstrual Dysphoric Disorder (PMDD)

Overview of the Study Design

In a three-arm, parallel, randomized, multicenter, placebo-controlled, double-blinded study, the efficacy and safety of continuous oral contraceptive therapy as a ninety-one day regimen (84 days active combination therapy followed by low dose estrogen for 7 consecutive days (DP3-91)), or as a twenty-eight day regimen (21 day active combination therapy followed by low dose estrogen for 7 consecutive days (DP3-28)), in combination with fluoxetine hydrochloride administered for approximately 6 consecutive months to women diagnosed with PMS and/or PMDD who desire contraception, will be evaluated.

A cohort of approximate 40-100 patients enrolled in each of the study arms will undergo endometrial biopsy (to test incidence of hyperplasia and carcinoma) prior to the initiation of study drug therapy and at the conclusion of the study or withdrawal.

Efficacy of the 28-day and 91-day regimens on premenstrual symptomatology will be measured by psychometric scales that include self-administered Visual Analogue Scales (VAS) and a prospective daily symptoms chart to evaluate psychological and somatic symptoms. The VAS measures tension, irritability, dysphoria, sleeping and eating patterns, headache, bloating, pain and breast tenderness and weight gain symptoms. Total score of the psychological and somatic symptoms will be computed. The patient and blind observer will also complete the PMTS at each visit.

Study Population

Females ages 18 through 49 who are fluent in English and capable of giving informed consent, without contraindication to the use of oral contraceptives and selective serotonin reuptake inhibitors (SSRIs), and meet the criteria for PMS including PMDD as defined in the diagnostic and statistical manual of mental disorders (DSM-IV). All patients will be counseled at the beginning of the study and at each study visit to use an alternative form of contraception. All patients will be followed for the occurrence of pregnancy during the course of the study. Patients who become pregnant during the course of the study will be followed for eight weeks following delivery or termination of the pregnancy. Infants will be followed for eight weeks following delivery.

Dosage

Patients will be randomized to one of the following:

(1) Ninety-one day oral contraceptive therapy with ethinyl estradiol (DP3-91) and fluoxetine hydrochloride administered for two cycles where each cycle consists of: 150 µg levonorgestrel and 30 µg ethinyl estradiol (days 1-84 of the first cycle and days 92-175 of the second cycle, 30 µg ethinyl estradiol (days 85-91 of the first cycle and days 176-182 of the second cycle), 20 mg fluoxetine hydrochloride (days 1-182), and placebo to preserve blinding (days 183-196);

(2) Twenty-eight day oral contraceptive therapy with ethinyl estradiol (DP3-28) administered for 7 cycles where each cycle consists of: 150 µg levonorgestrel and 30 µg ethinyl estradiol (days 1-21 for seven cycles), 30 µg ethinyl estradiol (days 22-28 for seven cycles), and 20 mg fluoxetine hydrochloride (days 1-196); or (3) Fluoxetine hydrochloride administered daily for 196 days: 20 mg fluoxetine hydrochloride per day (days 1-196) or placebo to preserve blinding (days 1-196).

Study Management

The study will utilize electronic case report forms and remote system management. Each investigator will be provided a programmed laptop computer dedicated to the study. This system allows the investigator to download and view patient diary data during clinic visits and also allows for rapid data queries by the study monitors. The system will also allow real-time on-line tracking of study site accrual rates, serious adverse events, pregnancies and study progress.

Outcomes Measurement Scales

The primary outcome will be defined as reduction in symptoms of PMS including PMDD as measured by the mean scores on Visual Analogue Scales (VAS) and the Premenstrual Tension Syndrome Scale (PMTS). The VAS will measure tension, irritability, dysphoria, sleeping and eating patterns, headache, bloating, pain and breast tenderness symptoms. Patients will be prompted to rate how they feel each day using 100 mm scales in which the descriptors range from "no symptoms" (0 mm) to "severe or extreme symptoms" (100 mm). The PMTS consists of a 36 item scale that will be completed by the patient and a 10-item scale completed by the blinded observer. Both scales rate premenstrual symptoms for a particular day; the total score can range from 0 (no symptoms) to 36 (all symptoms present and severe).

The secondary outcome will be defined as reduction in symptoms of PMS including PMDD as measured by the sub-score of somatic symptoms on VAS. The VAS will measure headache, bloating, pain and breast tenderness and weigh gain symptoms. Patients will be prompted to rate how they feel each day using 100 mm scales in which the descriptors range from "no symptoms" (0 mm) to "severe symptoms" (100 mm). In addition to information recorded in paper diaries, a standardized questionnaire will be used to determine whether the patient had any side effects.

Statistical Analysis

For the primary analysis, the mean of the VAS scales will be derived to obtain a single VAS score, which evaluates composite psychological and symptomatic outcomes. Mean percent reduction from baseline at the luteal phase will be compared using an analysis of covariance (ANCOVA) approach that evaluates the effects of the treatment group, center and treatment-by-center interaction, after adjusting for the effect of the baseline VAS score. All statistical tests will be two-sided at the 0.05 level of significance. Pairwise comparisons will be made for each active treatment to placebo. Secondary analyses will include a set of statistical tests for the PMTS and 10-item blinded observer-based measures.

Application of the compounds, compositions and methods of the present invention for the medical or pharmaceutical uses described can be accomplished by any clinical, medical, and pharmaceutical methods and techniques as are presently or prospectively known to those skilled in the art. It will therefore be appreciated that the various embodiments which have been described above are intended to illustrate the invention and various changes and modifications can be made in the inventive method without departing from the spirit and scope thereof.

What is claimed is:

1. A preparation comprising (a) 81 to 89 dosage forms comprising a combination of estrogen and progestin; and (b) 2 to 8 dosage forms consisting essentially of estrogen, wherein:
   the estrogen in each of the 81 to 89 dosage forms comprising the combination of estrogen and progestin in (a) is present in an amount equivalent to about 10 μg to about 50 μg of ethinyl estradiol;
   the estrogen in each of the 2 to 8 dosage forms consisting essentially of estrogen in (b) is present in an amount equivalent to about 5 μg to about 10 μg ethinyl estradiol; and
   the progestin in each of the dosage forms comprising the combination of estrogen and progestin in (a) is present in an amount of about 50 μg to about 150 μg of levonorgestrel.

2. The preparation of claim 1, wherein the estrogen in the each of the 81 to 89 dosage forms comprising the combination of estrogen and progestin in (a) is present in an amount equivalent to about 10 μg to about 30 μg of ethinyl estradiol.

3. The preparation of claim 1, wherein the estrogen in each of the 81 to 89 dosage forms comprising the combination of estrogen and progestin in (a) is present in an amount equivalent to about 30 μg of ethinyl estradiol.

4. The preparation of claim 1, wherein the estrogen in each of the 2 to 8 dosage forms consisting essentially of estrogen in (b) is present in an amount equivalent to about 10 μg ethinyl estradiol.

5. The preparation of claim 1, wherein the progestin in each of the dosage forms comprising the combination of estrogen and progestin in (a) is present in an amount of about 150 μg of levonorgestrel.

6. The preparation of claim 1, wherein the preparation comprises 84 dosage forms in (a).

7. The preparation of claim 1, wherein the preparation comprises 5-8 dosage forms in (b).

8. The preparation of claim 1, wherein the preparation comprises 7 dosage forms in (b).

9. The preparation of claim 1, wherein the preparation comprises 84 dosage forms in (a) and 7 dosage forms in (b).

10. The preparation of claim 1, wherein the estrogen is ethinyl estradiol.

11. The preparation of claim 1, wherein the preparation further comprises an antidepressant.

12. The preparation of claim 11, wherein the antidepressant is present in combination with the 2 to 8 dosage forms consisting essentially of estrogen.

13. The preparation of claim 11, wherein the antidepressant is present in combination with 5 to 8 dosage forms consisting essentially of estrogen.

14. The preparation of claim 11, wherein the antidepressant is present in an amount equivalent to about 5 mg to about 120 mg of fluoxetine hydrochloride.

15. The preparation of claim 11, wherein the antidepressant is present in combination with one dosage form of the 2 to 8 dosage forms consisting essentially of estrogen.

16. The preparation of claim 11, wherein the antidepressant is fluoxetine hydrochloride.

17. The preparation of claim 1, wherein the dosage forms are tablets for oral administration.

18. The preparation of claim 1, wherein the dosage forms are transdermal dosage forms for transdermal administration.

19. The preparation of claim 1, wherein the dosage forms are for monophasic administration.

20. A preparation comprising (a) 84 dosage forms comprising a combination of estrogen and progestin; and (b) 7 dosage forms consisting essentially of estrogen, wherein:
   the estrogen in each of the 84 dosage forms comprising the combination of estrogen and progestin in (a) is present in an amount of about 10 μg to about 30 μg of ethinyl estradiol;
   the estrogen in each of the 7 dosage forms consisting essentially of estrogen in (b) is present in an amount of about 10 μg ethinyl estradiol;
   the progestin in each of the dosage forms comprising the combination of estrogen and progestin in (a) is present in an amount of about 50 μg to about 150 μg of levonorgestrel; and
   wherein the dosage forms in (a) and (b) are tablets for oral administration.

21. A preparation comprising (a) 84 dosage forms comprising a combination of estrogen and progestin; and (b) 7 dosage forms consisting essentially of estrogen, wherein:
   the estrogen in each of the 84 dosage forms comprising the combination of estrogen and progestin in (a) is present in an amount of about 30 μg of ethinyl estradiol;
   the estrogen in each of the 7 dosage forms consisting essentially of estrogen in (b) is present in an amount of about 10 μg ethinyl estradiol;
   the progestin in each of the dosage forms comprising the combination of estrogen and progestin in (a) is present in an amount of about 150 μg of levonorgestrel; and
   wherein the dosage forms in (a) and (b) are tablets for oral administration.

22. A preparation comprising (a) 81 to 89 dosage forms comprising a combination of estrogen and progestin; and (b) 2 to 8 dosage forms comprising estrogen without progestin, wherein:
   the estrogen in each of the 81 to 89 dosage forms comprising the combination of estrogen and progestin in (a) is present in an amount equivalent to about 10 μg to about 30 μg of ethinyl estradiol;
   the estrogen in each of the 2 to 8 dosage forms comprising estrogen without progestin in (b) is present in an amount equivalent to about 5 μg to about 10 μg ethinyl estradiol; and
   the progestin in each of the dosage forms comprising the combination of estrogen and progestin in (a) is present in an amount of about 50 μg to about 150 μg of levonorgestrel.

23. The preparation of claim 22, wherein the dosage comprising estrogen without progestin in (b) is a dosage consisting of estrogen and one or more pharmaceutically acceptable excipients.

24. A preparation comprising (a) 81 to 89 dosage forms comprising a combination of estrogen and progestin; and (b) 2 to 8 dosage forms comprising estrogen without progestin, wherein:

the estrogen in each of the 81 to 89 dosage forms comprising the combination of estrogen and progestin in (a) is present in an amount equivalent to about 30 µg of ethinyl estradiol;

the estrogen in each of the 2 to 8 dosage forms comprising estrogen without progestin in (b) is present in an amount equivalent to about 10 µg ethinyl estradiol; and the progestin in each of the dosage forms comprising the combination of estrogen and progestin in (a) is present in an amount of about 150 µg of levonorgestrel.

25. The preparation of claim 24, wherein the dosage comprising estrogen without progestin in (b) is a dosage consisting of estrogen and one or more pharmaceutically acceptable excipients.

26. A preparation comprising (a) 84 dosage forms comprising a combination of estrogen and progestin; and (b) 7 dosage forms comprising estrogen without progestin, wherein:

the estrogen in each of the 84 dosage forms comprising the combination of estrogen and progestin in (a) is present in an amount equivalent to about 10 µg to about 30 µg of ethinyl estradiol;

the estrogen in each of the 7 dosage forms comprising estrogen without progestin in (b) is present in an amount equivalent to about 5 µg to about 10 µg ethinyl estradiol; and the progestin in each of the dosage forms comprising the combination of estrogen and progestin in (a) is present in an amount of about 50 µg to about 150 µg of levonorgestrel.

27. The preparation of claim 26, wherein the dosage comprising estrogen without progestin in (b) is a dosage consisting of estrogen and one or more pharmaceutically acceptable excipients.

28. A preparation comprising (a) 84 dosage forms comprising a combination of estrogen and progestin; and (b) 7 dosage forms comprising estrogen without progestin, wherein:

the estrogen in each of the 84 dosage forms comprising the combination of estrogen and progestin in (a) is present in an amount equivalent to about 30 µg of ethinyl estradiol;

the estrogen in each of the 7 dosage forms comprising estrogen without progestin in (b) is present in an amount equivalent to about 10 µg ethinyl estradiol; and the progestin in each of the dosage forms comprising the combination of estrogen and progestin in (a) is present in an amount of about 150 µg of levonorgestrel.

29. The preparation of claim 28, wherein the dosage comprising estrogen without progestin in (b) is a dosage consisting of estrogen and one or more pharmaceutically acceptable excipients.

30. A kit comprising the preparation of claim 1, wherein the dosage forms are arranged in a fixed sequence that corresponds to the stages of daily administration.

* * * * *